(12) United States Patent
Kuehn et al.

(10) Patent No.: US 7,569,062 B1
(45) Date of Patent: Aug. 4, 2009

(54) MITRAL AND TRICUSPID VALVE REPAIR

(75) Inventors: Stephen T. Kuehn, Woodbury, MN (US); Thomas F. Hinnenkamp, White Bear Lake, MN (US); William R. Holmberg, New Richmond, WI (US); Darrin J. Bergman, Shoreview, MN (US); Terry L. Shepherd, Shoreview, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/694,293

(22) Filed: Oct. 23, 2000

Related U.S. Application Data

(63) Continuation-in-part of application No. 09/115,820, filed on Jul. 15, 1998, now Pat. No. 6,165,183.

(51) Int. Cl.
*A61B 17/10* (2006.01)
(52) U.S. Cl. .................. 606/139; 623/2.11; 623/2.12
(58) Field of Classification Search ................ 606/139, 606/151, 153, 157
See application file for complete search history.

(56) References Cited

U.S. PATENT DOCUMENTS

| | | | | |
|---|---|---|---|---|
| 2,470,327 | A | * | 5/1949 | Tener ............................ 29/232 |
| 3,671,979 | A | * | 6/1972 | Moulopoulos ............. 623/2.11 |
| 3,874,388 | A | * | 4/1975 | King et al. ................... 606/213 |
| 3,916,908 | A | * | 11/1975 | Leveen ........................ 606/157 |
| 4,038,987 | A | | 8/1977 | Komiya ....................... 128/321 |
| 4,605,002 | A | * | 8/1986 | Rebuffat ...................... 606/148 |
| 4,655,218 | A | * | 4/1987 | Kulik et al. ................. 606/207 |
| 5,181,919 | A | * | 1/1993 | Bergman et al. ............ 606/139 |
| 5,403,326 | A | | 4/1995 | Harrison et al. |
| 5,425,738 | A | * | 6/1995 | Gustafson et al. ........... 606/151 |
| 5,453,086 | A | | 9/1995 | Weber |
| 5,478,353 | A | * | 12/1995 | Yoon ........................... 606/104 |
| 5,496,310 | A | | 3/1996 | Exconde et al. |
| 5,549,122 | A | * | 8/1996 | Detweilwer .................. 128/898 |
| 5,578,076 | A | * | 11/1996 | Krueger et al. .............. 623/2.11 |
| 5,601,572 | A | * | 2/1997 | Middleman et al. .......... 606/139 |
| 5,609,598 | A | | 3/1997 | Laufer et al. |

(Continued)

FOREIGN PATENT DOCUMENTS

DE       4319829       6/1993

(Continued)

OTHER PUBLICATIONS

Office Action from European Patent Office dated Feb. 25, 2008 in connection with corresponding EP Application No. 99 928 841.8-2310.

*Primary Examiner*—Todd E Manahan
*Assistant Examiner*—Victor X Nguyen
(74) *Attorney, Agent, or Firm*—Westman, Champlin & Kelly, P.A.; Hallie A. Finucane

(57) ABSTRACT

A novel approach to mitral or tricuspid valve repair involves the performance of an edge-to-edge fastening/securing of opposing heart valve leaflets through a catheter entering the heart. Thus, a device is introduced including a leaflet fastener applicator through a cardiac catheter or other suitable catheter. The leaflet fastener applicator and cardiac catheter can be formed into a kit. A gripper can be used to hold the heart valve leaflets while they are fastened.

23 Claims, 14 Drawing Sheets

U.S. PATENT DOCUMENTS

| | | | |
|---|---|---|---|
| 5,618,307 A | | 4/1997 | Donlon et al. |
| 5,702,048 A | * | 12/1997 | Eberlin .................... 227/177.1 |
| 5,732,872 A | | 3/1998 | Bolduc et al. |
| 5,810,847 A | * | 9/1998 | Laufer et al. ................ 606/108 |
| 5,855,614 A | * | 1/1999 | Stevens et al. .............. 128/898 |
| 5,891,162 A | * | 4/1999 | Sugarbaker et al. ......... 606/151 |
| 5,954,731 A | | 9/1999 | Yoon |
| 5,957,936 A | | 9/1999 | Yoon et al. |
| 5,976,164 A | * | 11/1999 | Bencini et al. .............. 606/159 |
| 6,017,358 A | | 1/2000 | Yoon et al. |
| 6,019,790 A | * | 2/2000 | Holmberg et al. .......... 623/2.11 |
| 6,086,600 A | | 7/2000 | Kortenbach |
| 6,120,513 A | * | 9/2000 | Bailey et al. ................ 606/139 |
| 6,165,183 A | * | 12/2000 | Kuehn et al. ................ 606/139 |
| 6,269,819 B1 | * | 8/2001 | Oz et al. ..................... 128/898 |
| 6,695,866 B1 | * | 2/2004 | Kuehn et al. ................ 606/213 |

FOREIGN PATENT DOCUMENTS

| | | |
|---|---|---|
| GB | 2 305 627 A | 4/1997 |
| WO | WO 98/33443 | 8/1998 |
| WO | 9920183 | 10/1998 |
| WO | WO 99/40851 | 8/1999 |

\* cited by examiner

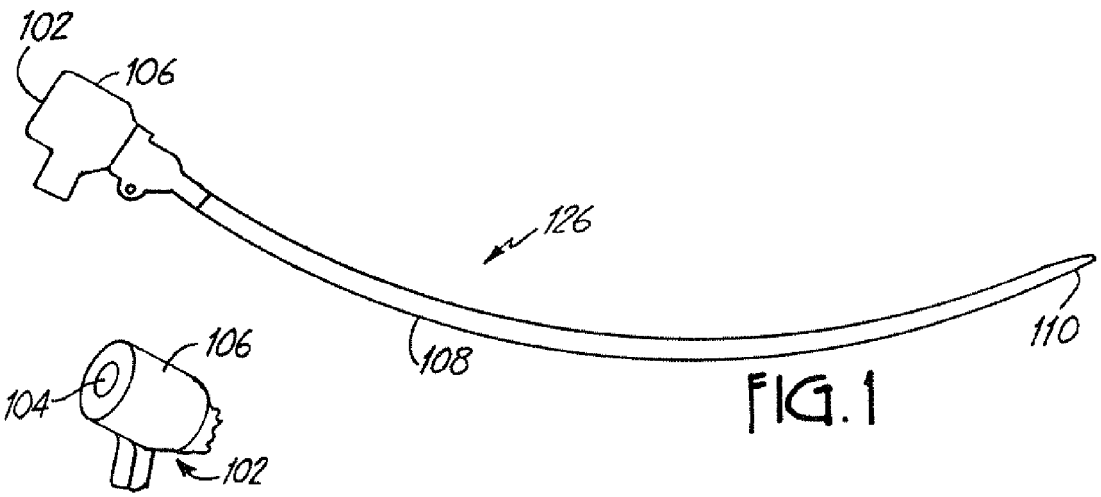
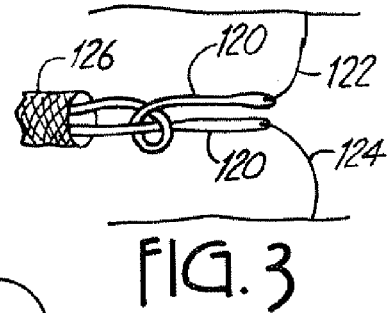
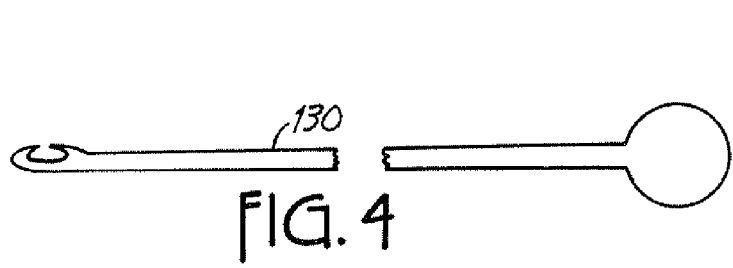
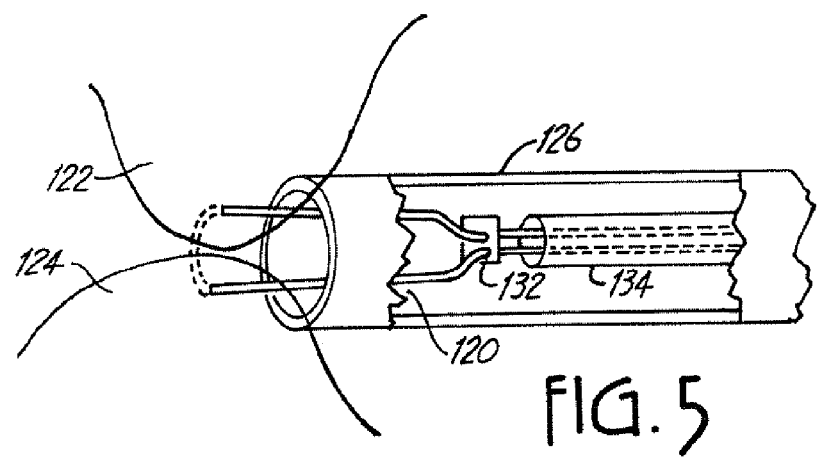

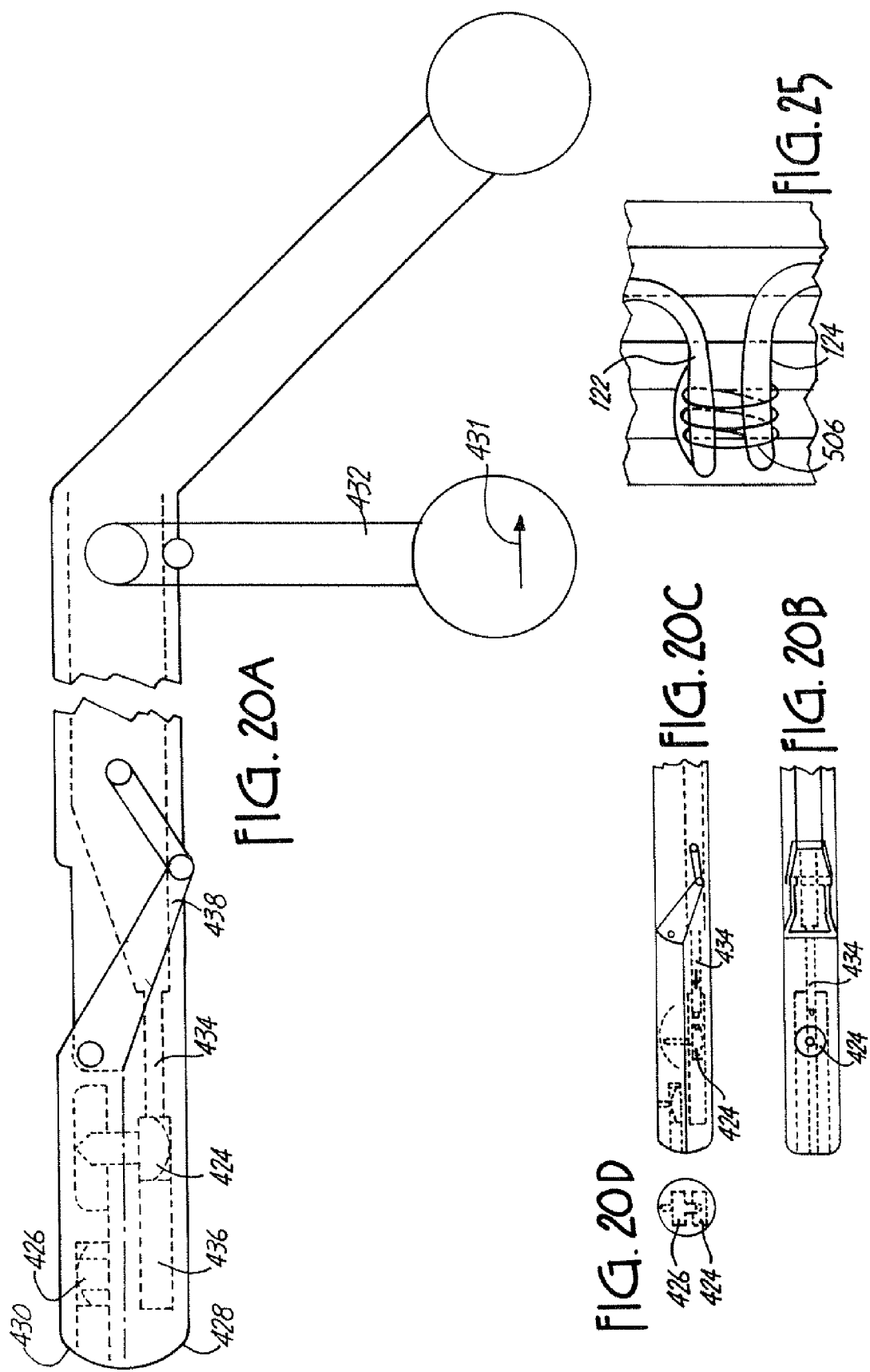

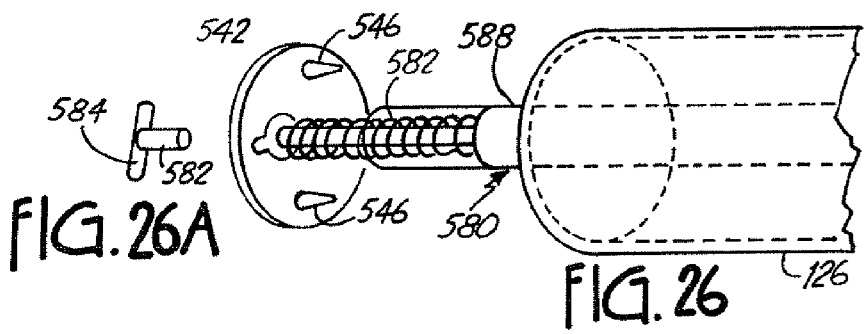
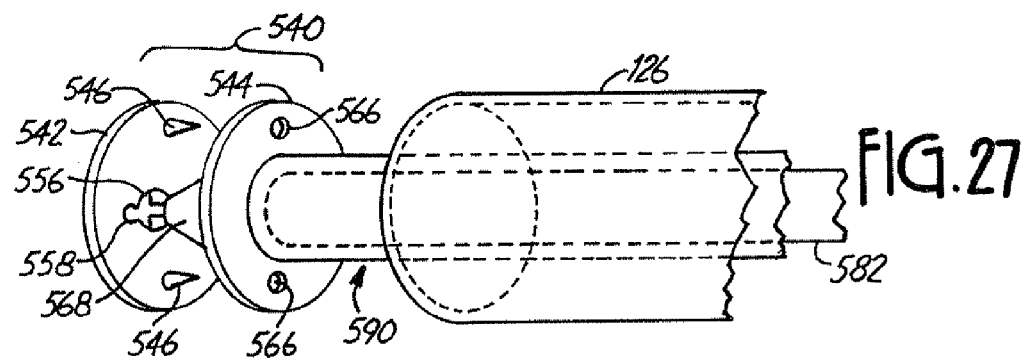
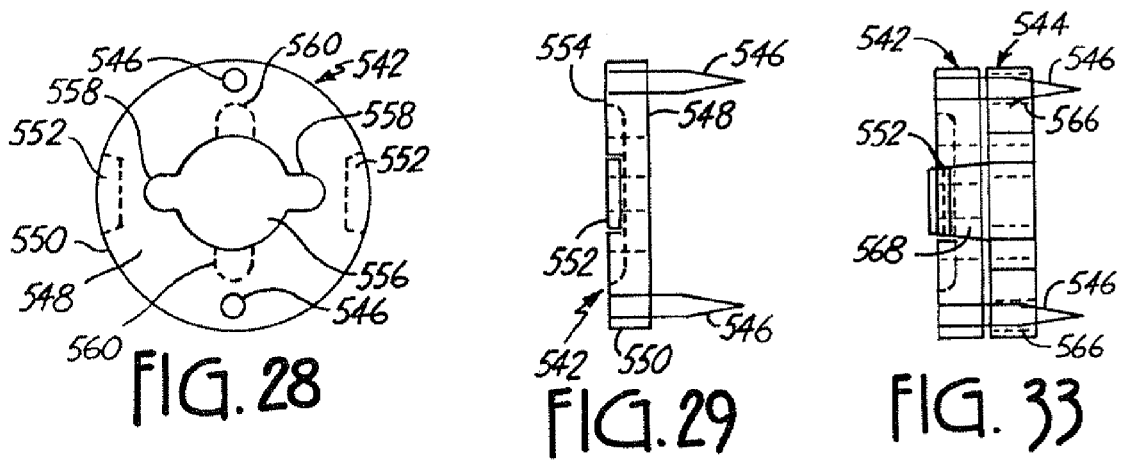
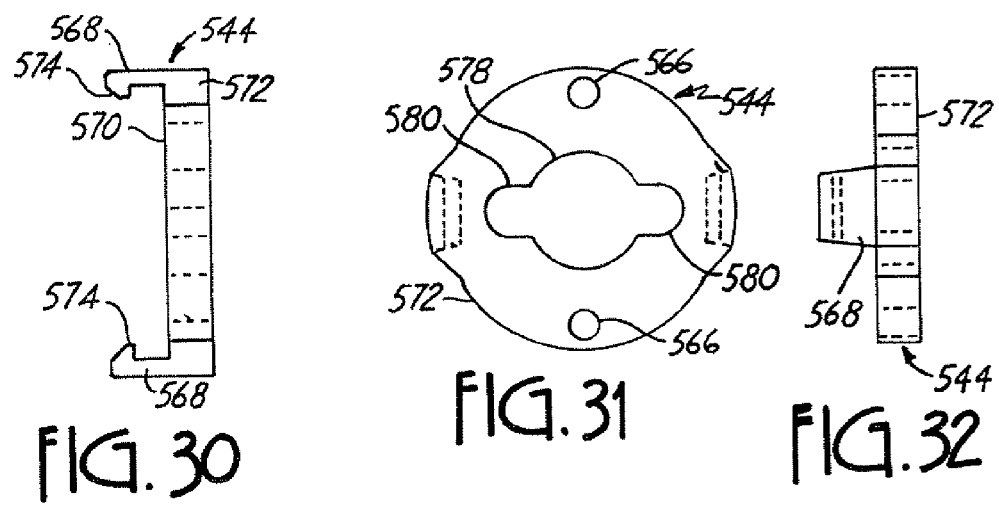

MITRAL AND TRICUSPID VALVE REPAIR

CROSS REFERENCE TO RELATED APPLICATIONS

This application is a continuation-in-part of U.S. application Ser. No. 09/115,820 filed Jul. 15, 1998 now U.S. Pat. No. 6,165,183 to Kuehn et al., entitled "Mitral and Tricuspid Valve Repair," incorporated herein by reference.

BACKGROUND OF THE INVENTION

The invention relates to the repair of mitral and tricuspid valves exhibiting valve regurgitation. More particularly, the invention relates to apparatus and methods suitable for a less invasive repair of a mitral or tricuspid heart valve.

Mitral regurgitation, i.e., backward leakage of blood at the mitral heart valve, results in reduced pumping efficiency. Furthermore, compensatory mechanisms such as hypertrophy and dilation of the ventricle suggest early treatment to prevent progressive deterioration of ventricular function. Diagnosis of mitral regurgitation can be performed using visualization with transesophageal echocardiography or by echocardiography. In particular, defective leaflet coaptation and the site and direction of the regurgitant flow can be examined to evaluate likely modes of failure.

Mitral valve prolapse, i.e., myxomatous degeneration of mitral valve leaflets, is the most common cause of mitral regurgitation in North America. Rheumatic heart disease was the most common cause of mitral regurgitation in the U.S.A. thirty years ago and is still the most common cause of mitral regurgitation in developing countries. Chronic rheumatic heart disease results in retraction, deformity and rigidity of one or both mitral valve cusps as well as structural abnormalities in the commissures, chordae tendinae and papillary muscles. Ischemic mitral regurgitation (IMR), i.e., anemia of the valve tissue due to reduced arterial blood flow feeding the valve tissue, is the second most common cause of mitral valve regurgitation. Studies suggest that annular irregularities and posterior papillary muscle fibrosis with scarring of the underlying ventricular wall may be associated with IMR.

Many cases of mitral regurgitation can be repaired by modifications of the original valve in a procedure generally referred to as valvuloplasty. These repair procedures typically involve a full sternotomy and quadrangular resection of the anterior leaflet, while on cardiopulmonary bypass. Repairs can also involve reattachment of chordae tendinae, which tether the valve leaflets, or removal of leaflet tissue to correct misshapen or enlarged valve leaflets. In some cases, the base of the valve is secured using an annuloplasty ring. Valves that are heavily calcified or significantly compromised by disease may need to be replaced.

As an alternative to these repair techniques, an edge-to-edge suturing of the anterior and posterior mitral valve leaflets can be performed. Commonly referred to as a "bow-tie" repair, edge-to-edge suturing ensures leaflet coaptation without performing a quadrangular resection of the anterior leaflet. The bow-tie repair generally involves the use of a centrally located suture, although a suture can be placed close to a commissure, or multiple sutures can be used to complete the repair. A centrally placed suture creates a double orifice valve, which resembles a bow-tie.

The bow-tie repair procedure has been applied using invasive procedures by placing the patient on extracorporeal circulation. An incision is made to provide access into the left atrium of the heart. Following suturing, the atrium is closed. Such repairs can result in a significant decrease in mitral regurgitation along with a corresponding increase in the ejection fraction.

SUMMARY OF THE INVENTION

In a first embodiment, the invention pertains to a heart valve leaflet fastener comprising two pairs of arms. Each pair of arms has a suitable size for fastening heart valve leaflets. The two pairs of arms are capable of fastening two adjacent leaflets. The arms pivot from one orientation to a gripping position with at least a portion of each respective paired arms being directed toward each other. The heart valve leaflet fastener can be incorporated into a kit along with a cardiac catheter and a fastener applicator. The cardiac catheter has suitable dimensions for deployment and insertion into a human heart in the vicinity of the mitral or tricuspid valve. The leaflet fastener has a size allowing insertion through the cardiac catheter. The fastener applicator is capable of releasably holding the leaflet fastener.

In a further embodiment, the invention pertains to a heart valve repair instrument comprising a ring and an applicator. The ring comprises two pointed shafts. The applicator can apply a force to the ring to deform the ring to bring the points of the shafts toward each other relative to an initial position. The ring and applicator have an appropriate size for placement within a chamber of a human heart.

In another aspect, the invention pertains to a heart valve repair instrument comprising a shaft, a cap, a gripper and a flexible rod, wherein the gripper comprises a plurality of arms radiating from a pivot with each arm having a spike. The cap is located distal to the pivot and the pivot is located distal to the shaft. The flexible rod connects to the cap to provide for movement of the cap relative to the gripper and the shaft by pulling the flexible rod. The cap has an opening that can be inserted over the pivot to lock the arms in a closed position.

BRIEF DESCRIPTION OF THE DRAWINGS

FIG. 1 is a side view of one embodiment of a cardiac catheter.

FIG. 2 is a perspective view of the proximal end of the cardiac catheter of FIG. 1.

FIG. 3 is a side view of a suture knot securing two leaflets together.

FIG. 4 is a side view of a knot pusher.

FIG. 5 is a perspective view of sutured heart valve leaflets being secured with a suture clip with a portion of a cardiac catheter cut away to expose structure within the catheter.

FIGS. 20A-C are sectional views of the fastener applicator of FIG. 18 where the section in FIG. 20B is taken at a right angle relative to the sections in FIGS. 20A and 20C. Hidden structures are shown with phantom lines.

FIG. 20D is a side view of the tack and cap of FIG. 20A secured together, shown in phantom.

FIG. 25 is a side view of heart valve leaflets secured with a spring fastener of FIG. 24.

FIG. 26 is a perspective view of a portion of a clip button held by a deployment device, the clip button being useful for fastening heart valve leaflets.

FIG. 26A is a perspective view of the tip of a first applicator.

FIG. 27 is a perspective view of the clip button of FIG. 26 and associated deployment devices, with the two portions of the clip button aligned.

FIG. 28 is a front view of a first portion of the clip button of FIG. 27.

FIG. 29 is a side view of the first portion of the clip button of FIG. 27.

FIG. 30 is a side view of the second portion of the clip button of FIG. 27.

FIG. 31 is a rear view of the second portion of the clip button of FIG. 27.

FIG. 32 is a side view of the second portion of the clip button of FIG. 27 rotated 90 degrees relative to the view in FIG. 30.

FIG. 33 is a side view of the two portions of the clip button of FIG. 27 fastened together.

DETAILED DESCRIPTION OF THE PREFERRED EMBODIMENTS

Figure 6:
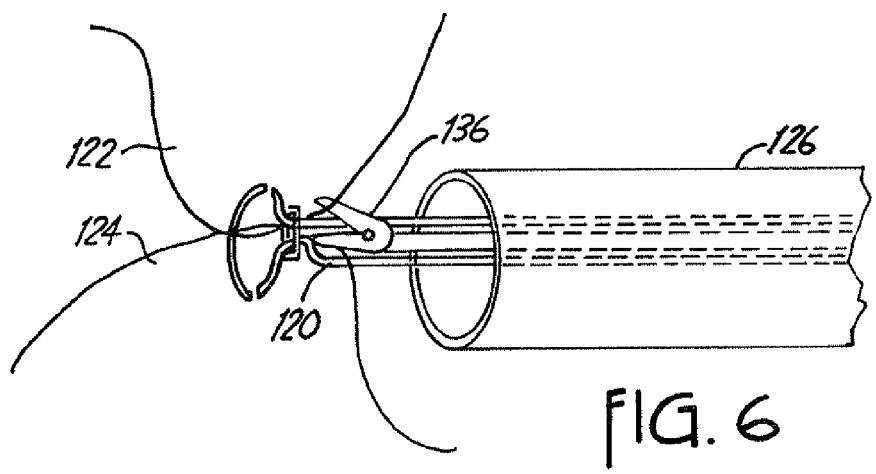
FIG. 6 is a perspective view of endoscopic scissors being used to cut a suture.

Methods have been developed for performing less invasive mitral valve repairs. While the discussion focuses on the repair of mitral heart valves, the repair approaches can be used for the repair of tricuspid valves using straightforward modification of the described procedures and instruments. In particular, the repairs can be performed on a beating heart such that the patient does not have to be placed on cardiopulmonary bypass.

Access into the heart for mitral valve repair is obtained by securing a passageway from the exterior of the body into the body and into the heart to provide access into the left atrium or left ventricle. With suitable instruments inserted through the passageway, the mitral leaflets are grabbed, and the edges of the leaflets are secured together. The gripping and securing or fastening procedures can be performed simultaneously in some embodiments of the invention, or they can be performed separately. A suitable method of visualization may be used to guide the manipulations. Manipulations to the mitral valve can be conducted under ultrasound or fluoroscopy to show correct placement of the devices and of the repair and to verify effectiveness of the repair.

One approach to introduce the instruments into the heart involves the direct introduction of a passageway through the wall of the heart. To introduce the passageway or a cardiac catheter into the body, a small incision is made in the chest. Instruments generally used to position catheters can be used to guide the cardiac catheter to the heart and into the heart wall, as described further below. Use of properly selected instruments for the introduction of the cardiac catheter reduces the amount of trauma to the heart. Upon completion of the mitral valve repair, the instruments are removed through the cardiac catheter, the cardiac catheter is removed, and the incision in the heart wall is repaired, for example, with suture.

Alternatively, the instruments can be introduced into the heart by a vascular approach. In these approaches, a catheter is introduced into an artery or vein and directed into the heart. These vascular approaches are described further below.

Suitable gripping and fastening instruments have appropriate dimensions to fit through the cardiac catheter into the heart. In general, the instruments have a tubular section or shaft between a distal end and a proximal end. The tubular section may be flexible. The distal end of the instrument is inserted through the cardiac catheter into the heart. The gripping and/or securing/fastening elements are located at the distal end of the instrument. One or more actuating elements are located at the proximal end.

In some embodiments, a single element performs the gripping and fastening functions. In other words, a fastening element grips the tissue during the fastening process such that a separately identifiable gripping element is not present. For example, suture can be placed through each leaflet such that tightening of the suture draws the two portions of the leaflets together.

Alternatively, the gripping and fastening elements can be distinct, separate instruments. For certain embodiments, functionally distinct gripping and fastening elements can be integrated into a single instrument such that a single tubular section is needed. Alternatively, the distinct gripping and fastening elements can be located on separate instruments, each having a separate tubular section. If the gripping and fastening elements are located on separate instruments, the tubular sections of the instruments can have suitable dimensions such that the two tubular sections can be inserted simultaneously through a single cardiac catheter. Alternatively, one or more additional cardiac catheters can be introduced into the heart to provide separate instrument passageways for the gripping and fastening instruments and any other instruments used to facilitate the procedure. Also, one or more additional cardiac catheters can be used to provide a means of direct visualization.

Instruments

The mitral valve repair device generally includes a gripper/fastener applicator instrument, and may include a cardiac catheter or other suitable catheter. The cardiac catheter generally has an elongated tubular section and proximal and distal ends each with an opening. For example, the cardiac catheter can be a catheter introducer used for standard intravascular placement or a similar instrument. An embodiment of a cardiac catheter 126 is displayed in FIG. 1. Proximal end 102 includes opening 104, as shown in FIG. 2, through which a gripper/fastener applicator instrument is introduced. Proximal end 102 preferably includes a hemostasis valve 106 to prevent blood from flowing out of the cardiac catheter. Standard designs used in the catheter art can be used for the hemostasis valve.

Tubular section 108 of cardiac catheter 100 preferably is flexible so that it can be guided through the body to the desired location. Generally, tubular section 108 has a length from about 4 cm to about 15 cm and a diameter from about 3 mm (9 French (F)) to about 10 mm (30 F), more preferably from about 3 mm (9 F) to about 8 mm (24 F). However, tubular section 108 can be selected to have a suitable length appropriate for the specific procedure used. Tubular section 108 preferably has a tapered end 110 to assist with introduction of cardiac catheter 100 into the heart.

Figure 18:
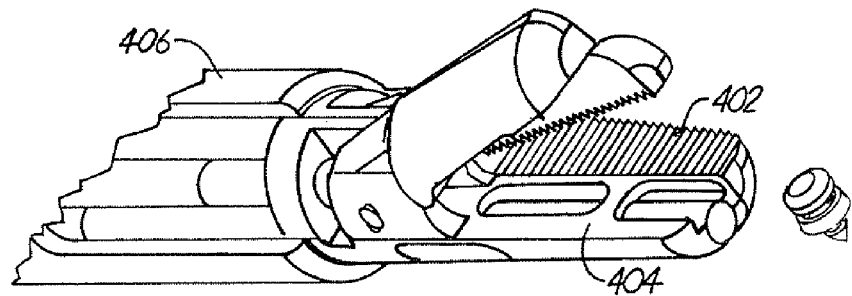
FIG. 18 is an enlarged perspective view of the gripper and fastener applicator of FIG. 17.

The gripper/fastener applicator instrument can have one functional element that accomplishes both the gripping and fastening operations simultaneously (e.g., FIG. 20), or two functional elements with one element performing the gripping and a second performing the fastening (e.g., FIG. 18). Two functional elements can be integrated together on a single instrument, or they can operate together as two separate instruments through the cardiac catheter(s). One or more cardiac catheters can be used, as needed or desired. Specific embodiments are described below.

A first type of gripper/fastener applicator has one functional device that accomplishes both gripping and fastening functions. Several embodiments of the first type of gripper/fastener applicator can be based on attachment of suture that is tied off to secure the leaflets together.

Referring to FIG. 3, sutures 120 placed through the respective valve leaflets 122, 124 can be tied outside of the body. Sutures 120 can be positioned using a needle or needles that are passed through leaflets and withdrawn through cardiac catheter 126. A knot pusher 130 (FIG. 4) can be used to push a knot tied outside of the body to the leaflets such that the knot pulls the leaflets together. Variations on the design of the needle and the knot pusher can be used to accomplish the same purposes. Alternatively, rather than tying a knot, a suture clip 132 can be used to fasten sutures 120, as shown in FIG. 5. Suture clip 132 is pushed into place up to leaflets 122, 124 with a clip pusher 134. Suture clip 132 is shaped such that suture can be fed through clip 132 only in one direction. Once sutures 120 are tied or clipped, suture 120 can be cut with endoscopic scissors 136, as shown in FIG. 6, or other similar device.

Figure 7:
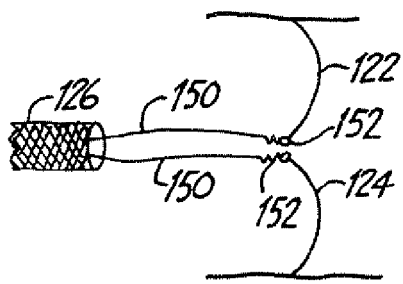
FIG. 7 is a perspective view of heart valve leaflets secured with attached wires that have suture attached at one end.

Another suture based gripper/fastener embodiment is depicted in FIG. 7. Instead of passing suture through each leaflet, the suture 150 can be secured to the edge of leaflets 122, 124 with a piece of wire 152 at one end of suture 150. Wire 152 can be sharpened spiral or coiled wire, such as a pacemaker lead. Wire 152 can be crimped on the edge of a particular leaflet 122, 124. As described above, the suture can be tied outside the heart, the knot can be pushed to the leaflets, and the suture 150 can be cut.

Figure 8:
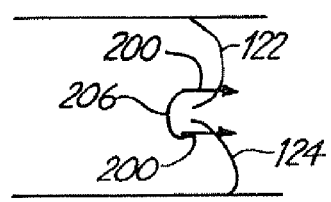
FIG. 8 is a side view of heart valve leaflets each pierced by a barbed needle where the barbed needles are attached to each other with suture.
Figure 9:
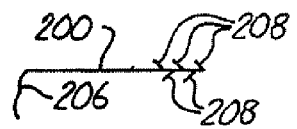
FIG. 9 is an enlarged view of a barbed needle of FIG. 8.
Figure 10:
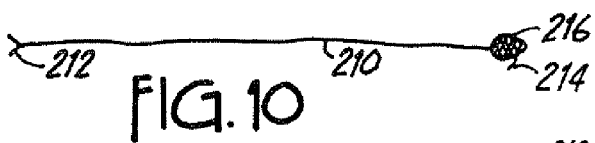
FIG. 10 is a side view of a push rod useful for the deployment of the barbed needles of FIG. 8.

Another embodiment of a single element gripper/fastener applicator involves the use of barbed needles. Referring to FIG. 8, a barbed needle 200 penetrates each leaflet 122, 124. If the repair requires further securing of the leaflets, additional needles may be deployed. Barbed needles 200 are connected to each other by suture 206. Each needle 200 can include a plurality of barbs 208 (FIG. 9). Barbed needles 200 can be deployed individually with a push rod 210 (FIG. 10). Push rod 210 generally has releasable jaws 212 for holding barbed needles 200 during deployment. Jaws 212 are activated by lever 214 at the handle end 216 of push rod 210. Alternatively, suitable push rods or other mechanical trigger actuators, such as spring activated mechanisms, can be used to deploy barbed needles 200.

Figure 11:
FIG. 11 is a side view of barbed needles with flexible wire attached to the needle.
Figure 12:
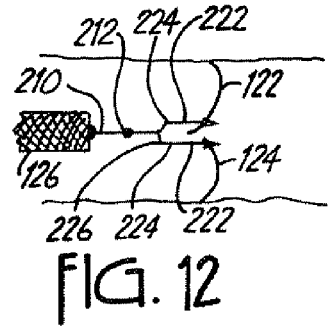
FIG. 12 is a side view of heart valve leaflets with the barbed needles of FIG. 11 piercing the heart valve leaflets and a push rod gripping the suture connecting the two barbed needles.

In order to use a short enough piece of suture 206 to hold the leaflets closed while having enough flexibility to deploy barbed needles 200, the embodiment in FIG. 8 can be modified as shown in FIG. 11. Each barbed needle 222 has a wire 224 extending from needle 222. Suture 226 connects the two wires 224. Barbed needles 222 can be deployed in the same way as depicted in FIG. 8. Referring to FIG. 12, push rod 210 with jaws 212 or a similar device can be passed into the heart through cardiac catheter 126 to grab suture 226. Push rod 210 is rotated to wind suture 226 and ultimately to wind wires 224. The winding of wires 224 draws barbed needles 222 closer together, resulting in leaflets 122, 124 being drawn closer together. Wires 224 preferably are made of material, such as stainless steel, which is malleable enough that they can be wound together with forces transmitted through the suture yet resilient enough that the wires do not unwind from the load transmitted by leaflets 122, 124.

Alternatively, suture can be connected directly to each barbed needle and looped around the other needle. Pulling each suture then draws each barb to the other. Additional knots can be pushed down from outside the body through cardiac catheter 126 to secure the two sutures together.

Figure 13A:
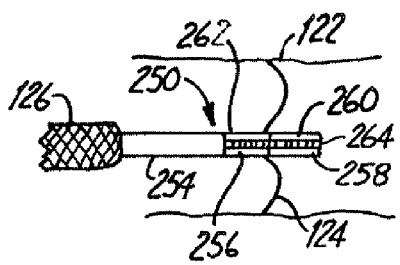
FIG. 13A is a side view of a fastener with a corresponding applicator inserted between two heart valve leaflets prior to deployment.
Figure 13B:
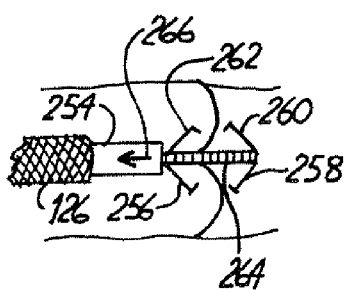
FIG. 13B is a side view of the fastener and applicator of FIG. 13A with arms extended on either side of the heart valve leaflets.

In other embodiments of a single element gripper/fastener applicator, a gripping/fastener applicator device is deployed and later released using an applicator. For example, referring to FIG. 13A, a deploying wand 250 is inserted through cardiac catheter 126. Outer sleeve 254 holds gripper arms 256, 258, 260, 262 in place against inner core 264. Deploying wand 250 is inserted between leaflets 122, 124. Referring to FIG. 13B, outer sleeve 254 is pulled away from gripper arms 256, 258, 260, 262 to permit gripper arms to extend once the outer sleeve 254 no longer holds them in place.

Figure 13C:
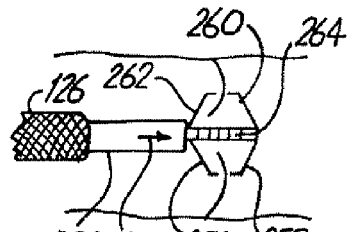
FIG. 13C is a side view of the fastener and applicator of FIG. 13A where the arms are being pushed together to grab the leaflets.
Figure 13D:
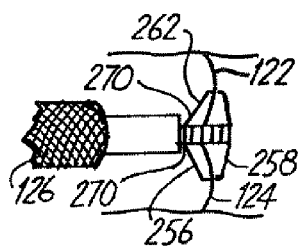
FIG. 13D is a side view of the fastener and applicator reaching a locked position where the leaflets are held firmly in place.
Figure 13E:
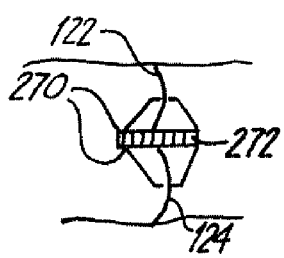
FIG. 13E is a side view of the leaflets secured in place by the fastener of FIG. 13A after the applicator is removed.
Figure 13F:
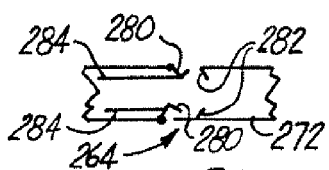
FIG. 13F is a sectional view of the engagement mechanism used to secure and detach the fastener of FIG. 13A from the applicator used to deploy the fastener.
Figure 14A:
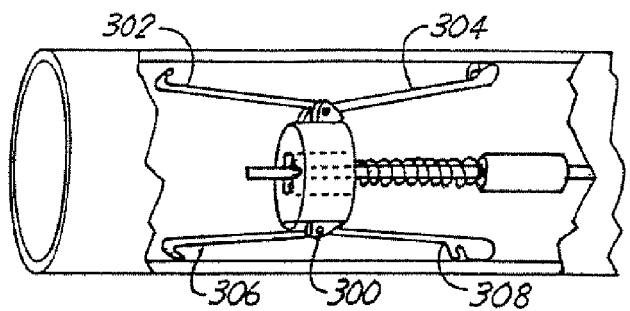
FIG. 14A is a perspective view of a gripper/fastener with spring loaded arms being deployed from a cardiac catheter with a portion of the cardiac catheter cut away to expose structure within the catheter.
Figure 14B:
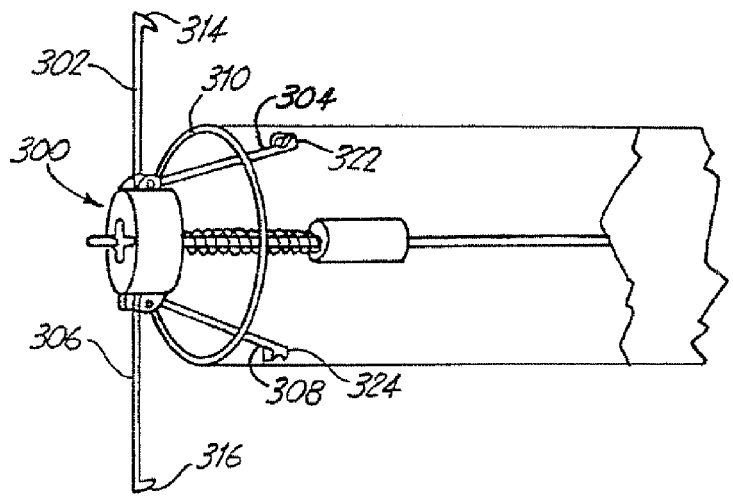
FIG. 14B is a perspective view of the gripper/fastener of FIG. 14A with two spring loaded arms being free of the cardiac catheter with a portion of the cardiac catheter cut away to expose structure within the catheter.
Figure 14C:
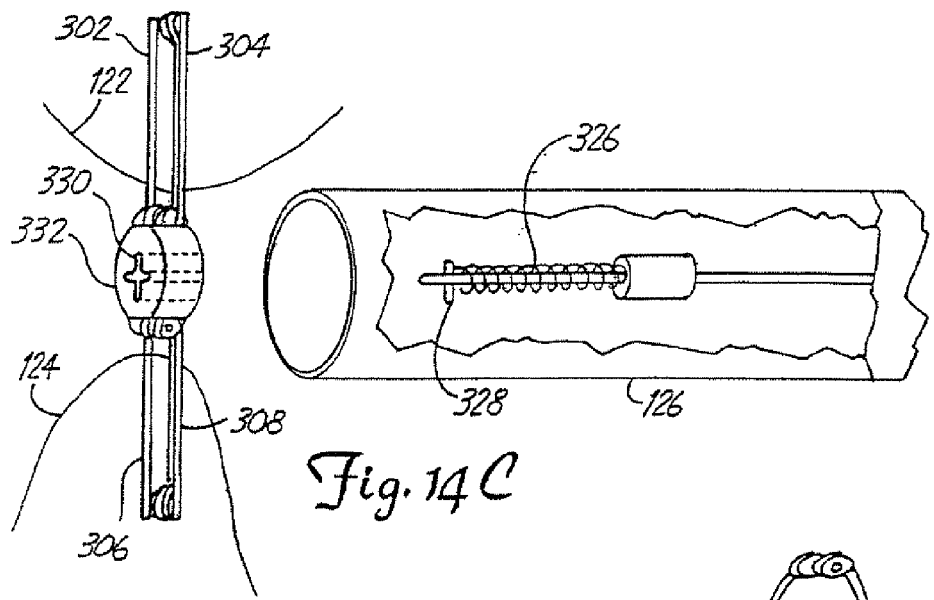
FIG. 14C is a perspective view of the spring loaded fastener of FIG. 14A deployed holding heart valve leaflets following release of the deployment device with a portion of the cardiac catheter cut away to expose structure within the catheter.
Figure 14D:
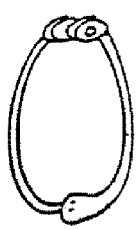
FIG. 14D is a perspective view of an alternative embodiment of the arms of the spring loaded fastener where the arms are curved.

With gripper arms 256, 258, 260, 262 extending on both side of leaflets 122, 124, inner core 264 is pulled inward and outer sleeve 254 is pushed outward in the direction of arrow 266 (FIG. 13C), such that arms are being pushed together to grab the leaflets. Referring to FIG. 13D, gripper arms 256, 258, 260, 262 hold leaflets 122, 124 in place. The position of gripper arms 256, 258, 260, 262 along inner core 264 is locked in place by stops 270. Gripper arms 256, 258, 260, 262 are extended beyond an equilibrium position such that restorative forces tend to pull gripper arms toward inner core 264. Referring to FIG. 13E, end 272 of inner core 264, while gripping and fastening leaflets 122, 124, is released from the remaining portions of inner core 264 by disengaging a locking mechanism thereby securing the leaflets with the fastening device. Inner core 264 is removed through cardiac catheter 126. The locking mechanism can have any of a variety of conventional structures, so as to grip and fasten leaflets 122, 124. One embodiment of a suitable locking mechanism is depicted in FIG. 13F. Pivoting latches 280 lock into flanges 282. Wires 284 can be used to release latches 280 from flanges 282. Gripper arms 256, 258, 260, 262 generally have a length from about 2 mm to about 10 mm. Inner core 264 generally has a diameter from about 1 mm to about 8 mm.

A similar embodiment of the invention is depicted in FIG. 14. In single element gripper/fastener applicator 300, arms 302, 304, 306, 308 are spring loaded. As arms 302, 304, 306, 308 are pushed free of the end 310 of cardiac catheter 126, they extend due to the spring loading feature. In FIG. 14B, gripper/fastener applicator 300 is depicted with arms 302, 306 extended. Arms 302, 306 have pointed tips 314, 316 that can pierce leaflets 122, 124. As depicted in FIG. 14C, once arms 304, 308 are free of the cardiac catheter 126, arms 304, 308 extend on one side of the leaflets to grasp leaflets 122, 124 along with arms 302, 306, which extend on the other side of leaflets 122, 124. Arms 304, 308 have clasps 322, 324 that engage pointed tips 314, 316 such that arms 302, 304, 306, 308 firmly grasp leaflets 122, 124 therebetween. Grasper/fastener applicator 300 is released from applicator 326 by rotating knob 328 such that knob 328 passes through passageway 330 within base 332. In an alternative embodiment, arms 302, 304, 306, 308 are curved as depicted in FIG. 14D.

Another alternative embodiment of a single element gripper/fastener applicator is shown in FIGS. 15A-15F. The gripper 340 comprises a cap 342 and a flexing spiked clip 344. Shaft 346 is used to deploy gripper 340 through cardiac catheter 126. A flexible rod 348 connects cap 342 through a passage in shaft 346 with the proximal end of cardiac catheter 126. Cap 342 includes an opening 350 that has a suitable size for the insertion and securing of a portion of spiked clip 344.

Flexing spiked clip 344 includes a plurality of leaflet gripping members 352. As shown in FIGS. 15A-15E, two leaflet gripping members 352 are included for gripping two leaflets of a valve, such as a mitral valve. In the embodiment shown in FIGS. 15B and 15C, each leaflet gripping member 352 includes two spiked arms 354 connected by a flexible support structure or web 356. Flexible support structure 356 provides added stability to this embodiment of the gripping member. Different numbers of leaflet gripping members or arms can be used, as appropriate. Alternatively, a leaflet gripping member may not have a support structure connecting the spiked arms. Arms 354 preferably include a spike 358 for gripping a leaflet. Arms 354 join at pivot element 360 which has a hole for the passage of flexible rod 348. Pivot element 360 can just be a joint at which arms 354 meet, although pivot element 360 can include a hinge. A hinge may include a spring to bias the arms in an extended position.

Arms 354 can move around pivot element 360 either due to the inclusion of a hinge at pivot element 360, a hinge with a spring at pivot element 360, or due to the resiliency of the materials used to form pivot element 360. In preferred embodiments, arms 354, support structures 356 and pivot element 360 are formed from biocompatible metals, such as stainless steel, spring metals, or memory metals, such as, Elgiloy®, a cobalt-chromium-nickel-molybdenum-iron alloy, MP35N, a nickel-cobalt-chromium-molybdenum alloy, and Nitinol®, a nickel-titanium alloy. Arms 354, support structures 356 and pivot element 360 preferably include the same metal. Support structures 356 can further include fabric or the like to cover the metal.

Shaft 346 includes a passage for flexible rod 348. Thus, flexible rod 348 extends from cap 342 to the proximal end of cardiac catheter 126. Shaft 346 further includes anchor 362 that secures strands 364. Strands 364 connect to arms 354 to limit the extension of arms 354 about pivot 360. Anchor 362 can include, for example, a weld, adhesive or the like, and shaft 346 can include a cut out to provide flexibility for the placement of anchor 362.

Figure 15A:
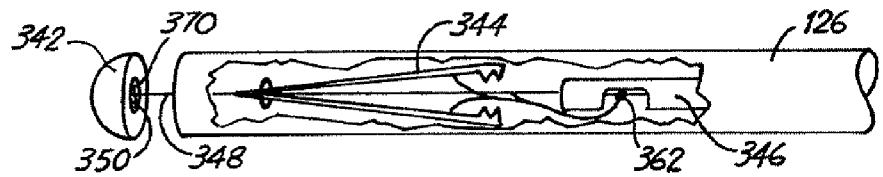
FIG. 15A is a cut away, perspective view of a fastener applicator including a fastener with moveable arms in a compressed configuration for deployment through a cardiac catheter, wherein a portion of the cardiac catheter is cut away to expose the fastener applicator.
Figure 15B:
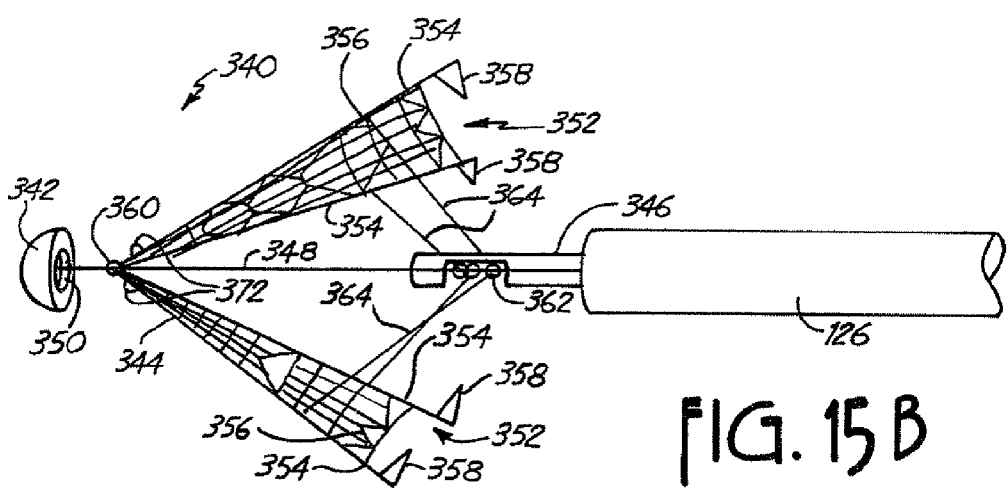
FIG. 15B is side perspective view of the fastener applicator of FIG. 15A wherein the arms are approaching an expanded configuration after clearing the cardiac catheter.
Figure 15C:
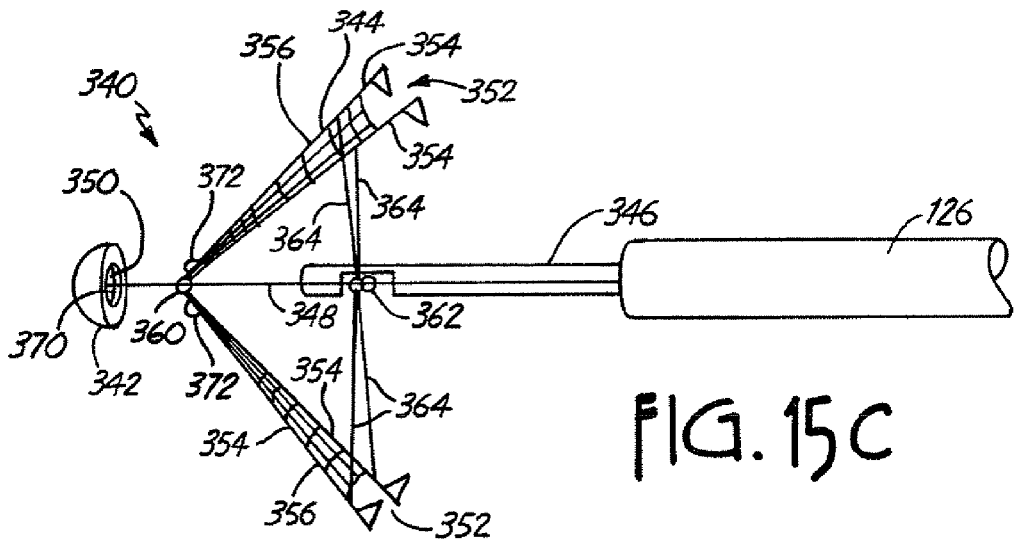
FIG. 15C is a side perspective view of the fastener applicator of FIG. 15A with the arms in the fully expanded configuration.

Referring to FIG. 15A, for deployment, the flexing spiked clip 344 can be folded into cardiac catheter 126. The cardiac catheter should be positioned to place the gripper beyond the heart valve leaflets. If cardiac catheter 126 is withdrawn toward its proximal end relative to shaft 346, flexing spiked clip 344 is released from cardiac catheter 126. Once released, arms 354 flex, as shown in FIG. 15B, to a more expanded configuration due to a spring placed at pivot 360, a hinge, or due to the use of memory metals that flex due to stresses within the metal. As shown in FIG. 15C, arms 354 reach a limiting position due to constraints applied by strands 364.

Figure 15D:
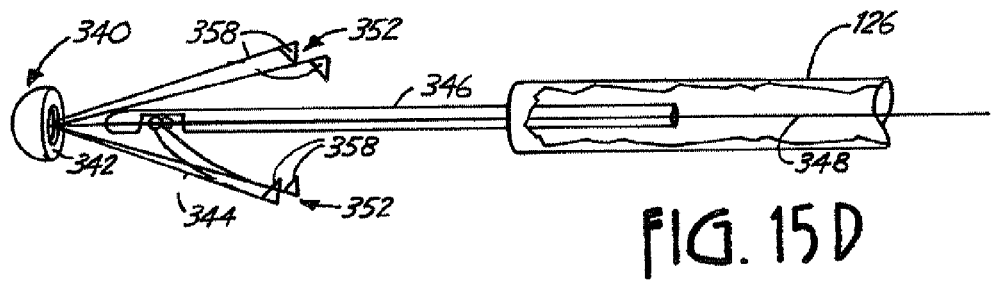
FIG. 15D is a side perspective view of the fastener applicator of FIG. 15A with its pivot partly inserted in a cap, with a portion of the cardiac catheter cut away.

Pulling on flexible rod 348 at the proximal end of cardiac catheter 126 pulls cap 342 against spiked clip 344 to drive spiked clip 344 against the leaflets, thereby impaling or otherwise gripping the leaflets with spikes 358. Further pulling on flexible rod 348 draws pivot 360 into opening 350 in cap 342, as shown in FIG. 15D. As pivot 360 is drawn into opening 350, arms 354 fold, which draws the leaflets toward each other.

Figure 15E:
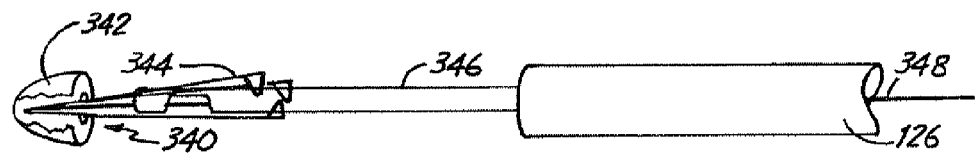
FIG. 15E is a side perspective view of the fastener applicator of FIG. 15A with the pivot locked within the cap, wherein a portion of the cap is cut away.
Figure 15F:
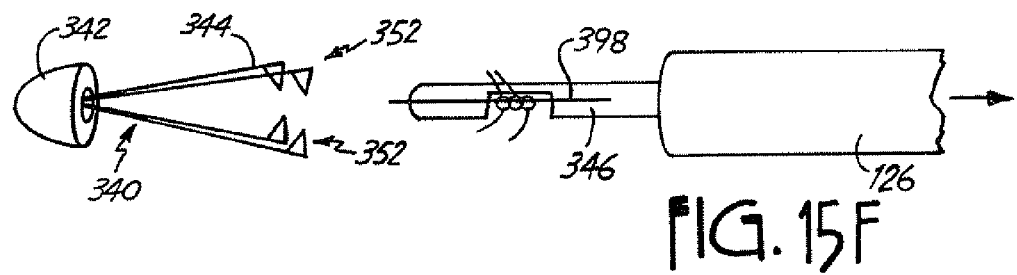
FIG. 15F is a side perspective view of the fastener applicator of FIG. 15A with a shaft disconnected from the cap to free the fastener.

Referring to FIG. 15E, spiked clip 344 becomes locked within cap 342 when pivot 360 is sufficiently drawn into cap 342. The expansive forces around pivot 360 hold the arms in the locked or closed position. In preferred embodiments, cap 342 includes a ridge 370 or similar locking mechanism that snaps over bumps 372 on arms 354 or, alternatively, on pivot 360 to secure cap 342 in a locked position, thereby fastening leaflets together. In alternative embodiments, cap 342 and arms 354 include mated threads as a locking mechanism, such that cap 342 can be screwed over the end of arms 354 by rotating flexible rod 348 to lock the cap in place, thereby fastening leaflets together. Referring to FIG. 15F, flexible rod 348 can be released using a disengaging mechanism, such as a latch mechanism, manipulated at the proximal end of cardiac catheter 126, such that cardiac catheter 126 and shaft 346 can be withdrawn. Suitable disengaging mechanisms include, for example, the bayonet structure shown in FIGS. 14A-14C for the release of gripper/fastener 300 from applicator 326.

Figure 15G:
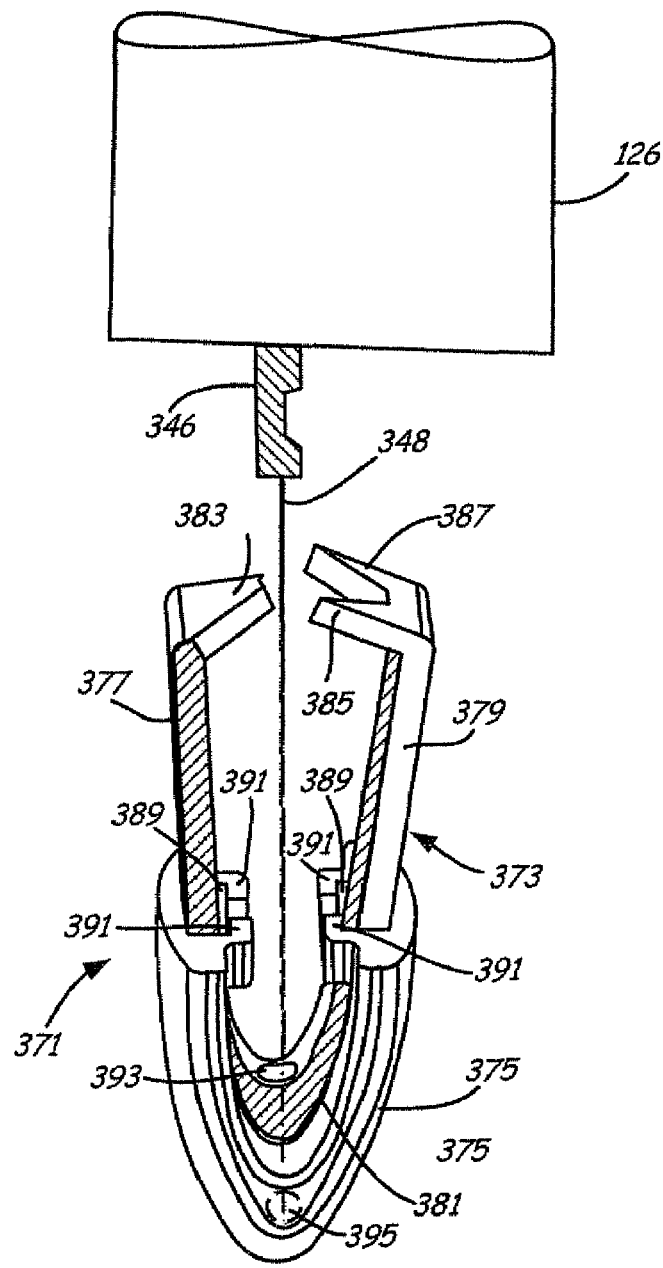
FIG. 15G is a side perspective view of an alternative embodiment of the fastener of FIG. 15A with one pair of arms.

A variation of the embodiment shown in FIGS. 15A-15F is shown in FIG. 15G. Gripper 371 includes a two armed clip 373 and a sliding cap 375. Clip 373 has two spiked arms 377, 379 extending from and moving around pivot member 381 either due to the inclusion of a hinge at pivot member 381, a hinge with a spring at pivot member 381 or due to the resiliency of the materials used to for pivot member 381. Spiked arm 377 has a single spike 383, and spiked arm 379 has two spikes 385, 387, or vice versa. Spikes 385, 387 have a gap between them to accommodate spike 383 when clip 373 is in folded orientation during deployment through cardiac catheter or while gripping the leaflets. Other mating arrangements of spikes 383, 385, 387 are contemplated. In addition, a different number of arms can be used, such as in FIGS. 15A-15F. Sliding cap 375 is preferably rigid, and cap 375 includes a groove 389 to accommodate clip 373. Stops 391 keep clip 373 within cap 375, such that cap 375 cannot completely slide off of clip 373. Clip 373 includes a hole 393 for the passage of flexible rod 348 to manipulate cap 375 from the proximal end of the cardiac catheter 126. Cap 375 also includes an anchor 395, shown in phantom lines, for the attachment of flexible rod 348.

Clip 373 opens to the fully open extended position as it is removed from cardiac catheter 126 and stays open due to a spring at pivot member 381, a hinge or resilience of the material at pivot member 381. When flexible rod 348 is pulled proximally toward catheter 126, arms 377, 379 collapse into cap 375 and grip and/or pierce the leaflets. The expansive forces around base 381 holds arms 377, 379 in the locked or closed position. Cap 375 can also include a locking mechanism similar to the embodiment in FIGS. 15A-15F to fasten the leaflets together. Release of the flexible rod 348 and catheter 126 is similar to that discussed for FIGS. 15A-15F.

The second type of gripper/fastener applicator has two distinct elements, a gripper element and a fastener applicator element. The gripper element and the fastener applicator element can be located at the respective distal ends of two distinct shafts. For certain embodiments the gripper element and the fastener applicator elements can be integrated on a single shaft and may be adapted to move relative to one another as appropriate for the procedure that is being performed, i.e., gripping or fastening. In this way, a single shaft can be guided through the cardiac catheter.

Figure 16:
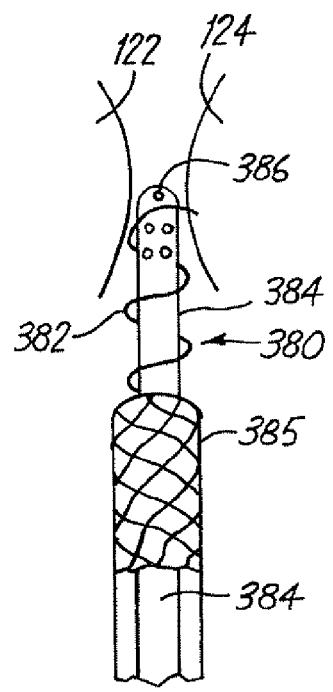
FIG. 16 is a side view of a needle fastener with a suction based gripper.

An embodiment of a distinct gripper and a fastener applicator integrated onto a single shaft is depicted in FIG. 16. Gripper/fastener applicator 380 has a spiral needle 382, which spirals around inner catheter 384. The first step involves applying suction through an internal lumen of inner catheter 384 by way of openings 386 to grasp and position a leaflet against inner catheter 384. Once the leaflets are grasped by suction, spiral needle 382 is advanced and rotated. Rotation of outer sleeve 388 results in the passage of spiral needle 382 through leaflets 122, 124. Spiral needle 382 is mounted on outer sleeve 388 that rotates around inner catheter 384. The outer sleeve can be threaded to provide appropriate pitch and number of rotations. To hold the leaflets in place, spiral needle 382 is disengaged from outer sleeve 388 by disengaging a clamp or the like at the end 390 of outer sleeve 388. If desired, the needle can be crimped to ensure permanent attachment. The suction based gripper of FIG. 16 can be used also with other types of fasteners.

Figure 17:
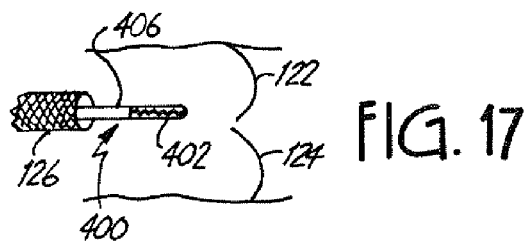
FIG. 17 is side view of a gripper mounted adjacent a fastener applicator being directed toward heart valve leaflets.

Referring to FIGS. 17-18, device 400 includes a gripper 402 and a fastener applicator 404 that extend from a shaft 406. Gripper 402 and fastener applicator 404 can be adjacent each other, as shown in FIG. 18. Alternatively, gripper 402 and fastener applicator 404 may move relative to each other by sliding in a tube, track, or similar mechanisms. The relative position of gripper 402 and fastener applicator 404 can be reversed. In FIG. 18, with fastener applicator 404 in a distal withdrawn position, gripper 402 can grab leaflets 122, 124. Then, fastener applicator 404 can be opened in the withdrawn position and slid forward to apply a tack on captured leaflet edges. Therefore, gripper 402 preferably is oriented relative to leaflets 122, 124 as shown in FIG. 17.

Figure 19A:
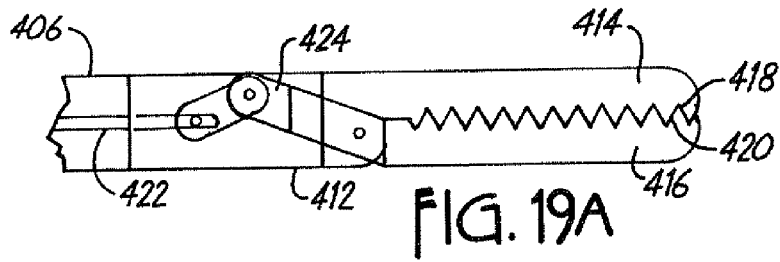
FIG. 19A is a sectional side view of the gripper of FIG. 18.

One embodiment of gripper 402 is depicted in FIG. 19A. In this embodiment, claw gripper 412 has opposing jaws 414, 416, which meet at serrated edges 418, 420 in a closed orientation. Serrated edges 418, 420 assist with the gripping of the leaflets 122, 124. The extension of rod 422 alters the relative position of jaws 414, 416 by moving a lever 424. Rod 422 extends through shaft 406 to the distal end of shaft 406 such that a physician can manipulate rod 422 outside of the patient. The length of jaws 414, 416 should be appropriate for the jaws to reach leaflets 122, 124 at the maximum anticipated spacing between leaflets 122, 124. If desired, grippers 412 can be used with a shaft separate from a shaft holding a fastener applicator element. Grippers 412 are designed to grip leaflets 122, 124 as depicted in FIGS. 17, 18 and 19.

Figure 19B:
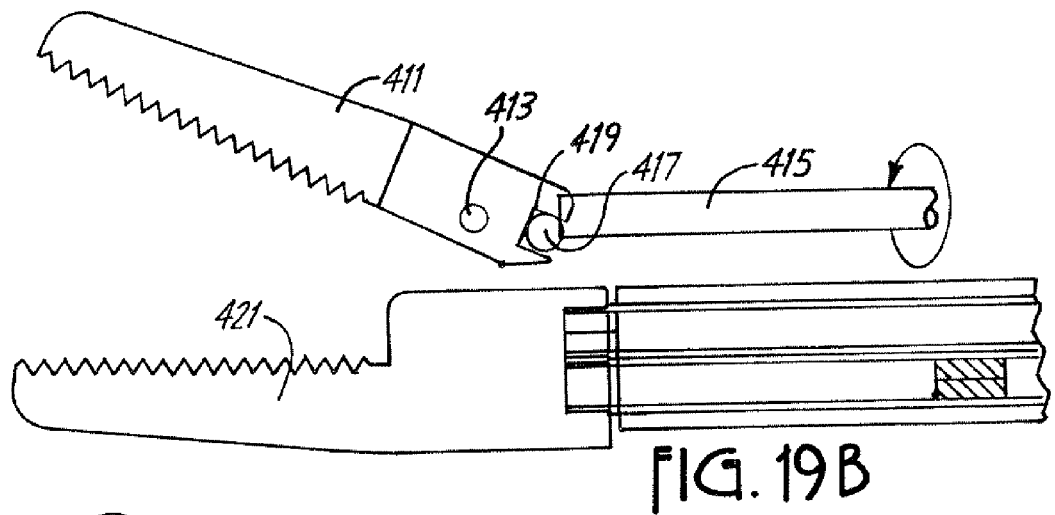
FIG. 19B is an exploded side view of an alternative embodiment of the gripper of FIG. 19A, the alternative embodiment being based on a cam, where the rod and moveable jaw have been removed from the remainder of the gripper.
Figure 19C:
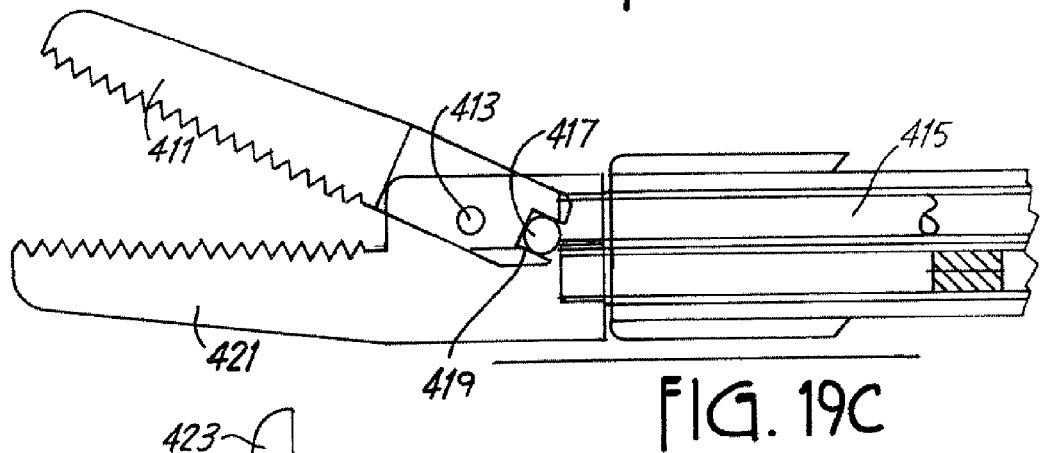
FIG. 19C is a side view of the embodiment shown in FIG. 19B.
Figure 19D:
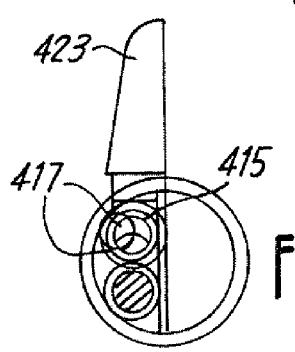
FIG. 19D is a view down the end of the shaft from the proximal end toward the jaws, where the ball of the cam is shown in both an open and closed position.

As an alternative to the lever mechanism shown in FIG. 19A, a cam can be used to rotate the jaw, as depicted in FIGS. 19B-D. In particular, jaw 411 rotates around pivot 413. Rotation of rod 415 causes ball 417 to change position relative to the position of rod 415. Ball 417 fits into track 419 in the end of jaw 411. Also, ball 417 fits into a notch in an off center position in the end of rod 415 such that rotation of rod 415 moves ball 417 up or down. Lowering of the ball results in the opening of jaw 411 relative to jaw 421. Rod 415 is rotated using lever 423, as shown in FIG. 19D. Generally a half rotation of rod 415 results in motion of jaw 411 from a closed position to its open position.

As depicted in FIG. 18, fastener applicator 404 applies a fastener, such as a tack. Further details about fastener applicator 404 can be seen in FIG. 20. Fastener applicator 404 holds tack 424 and cap 426 in separate housings for deployment. When jaws 428, 430 are opened by the movement of lever 432 in the direction shown by the arrow 431 in FIG. 20A, rod 434 slides tack 424 within track 436 to a position aligning cap 426 with tack 424, as shown in FIGS. 20B and 20C. Jaws 428, 430 rotate relative to each other by way of lever arm 438 or other mechanical link, such as a cam. When jaws 428, 430 subsequently are closed, tack 424 engages cap 426, as shown in FIG. 20D, thereby fastening leaflets 122, 124. Jaws 428, 430 can be opened to release tack 424 and fastened leaflets 122, 124.

Figure 21:
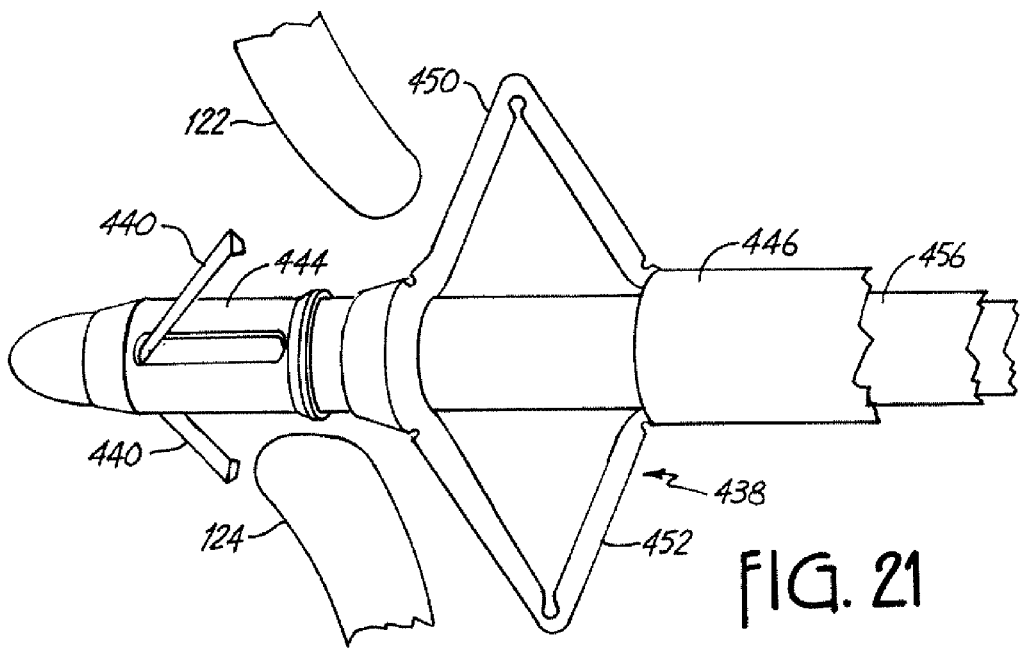
FIG. 21 is a side view of a gripper with a plunger used to direct the leaflets to gripper arms.
Figure 22:
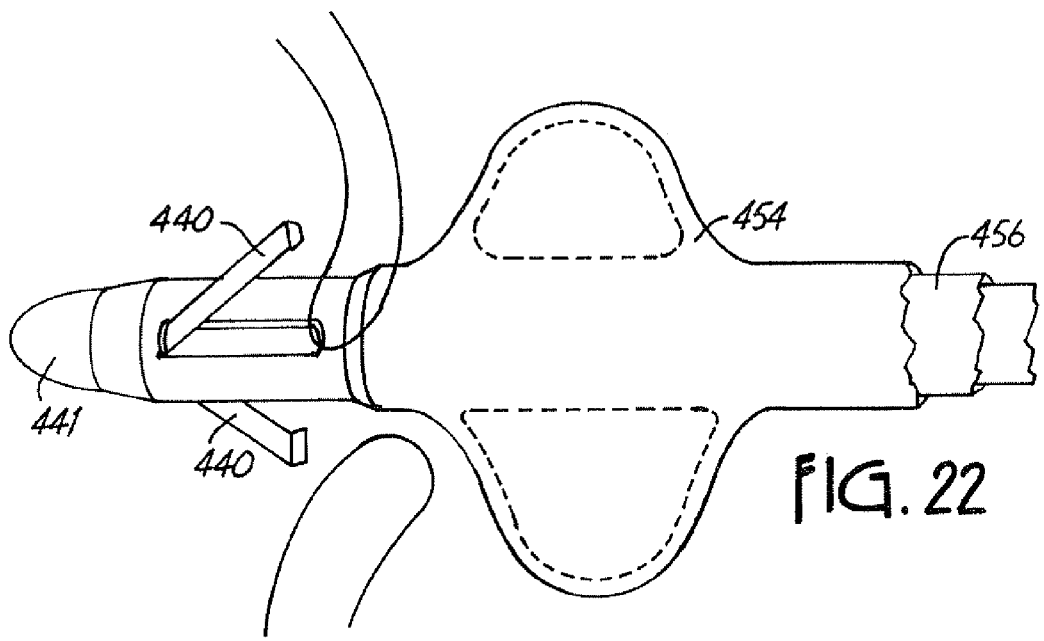
FIG. 22 is a side view of an alternative embodiment of a gripper with spring loaded arms and a balloon plunger that directs the leaflets to the spring loaded arms.

While the above grippers and fastener applicators can be used for an atrial or ventricular approach, other designs for the gripper are particularly adapted for gripping leaflets from an atrial approach. Referring to FIG. 21, gripper 438 includes graspers 440 used to grasp each leaflet 122, 124. To push the leaflets toward graspers 440, plunger 446 includes two or more arms 450, 452. In an alternative embodiment depicted in FIG. 22, a balloon plunger 454 is used. Balloon plunger 454 is deflated for delivery and removal of the instrument through cardiac catheter 126 and inflated within the heart for use to guide the leaflets to the graspers 440.

With either embodiment of the plunger, shaft 456 can be pulled to draw spring loaded graspers 440 toward plunger 446 or 454 to grip leaflets 122, 124 within grasper 440. Alternatively, plunger 446 or 454 can push leaflets 122, 124 toward graspers 440. In any case, as plunger 446 or 454 reaches a certain position relative to graspers 440 so that graspers 440 are within reach of leaflets 122, 124, shaft 456 is pulled back to retract graspers 440, which clasp leaflets 122, 124 between graspers 440 and grasper tube 441. Once leaflets 122, 124 are clasped, plunger 446, 454 can be removed. After leaflets 122, 124 are fastened, graspers 440 can be released by extending shaft 456 such that gripper 438 can be withdrawn. Graspers 440 should be less than about 10 mm in length. Graspers 440 can be curved.

Figure 23:
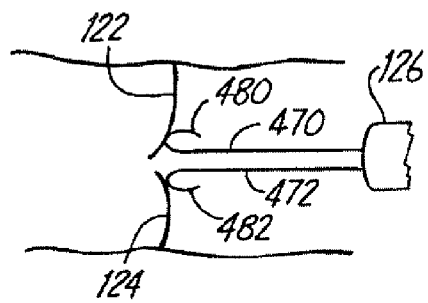
FIG. 23 is a side view of hooks used as gripper elements.

Another approach to grasping the leaflets from the atrial side is depicted in FIG. 23. Hooks 470, 472 are deployed through cardiac catheter 126 to grab leaflets 122, 124. Hooks 470, 472 preferably have sharp tips 480, 482 without barbs. With leaflets 122, 124 held in place, a variety of fasteners, as described throughout, can be used to fasten leaflets 122, 124. Once leaflets 122, 124 are fastened securely, hooks 470, 472 can be released and removed by pushing hooks 470, 472 to release the respective leaflets 122, 124 and rotating hooks 470, 472 such that they do not grab leaflets 122, 124 when withdrawn.

Once one embodiment of grasper is holding the leaflets, another type of grasper generally can be substituted for that grasper to hold the leaflets. A wider variety of graspers are suitable for grasping already held leaflets. In this way, a fastener applicator can be used with a more appropriate grasper, if desired. Furthermore, multiple grippers can be used to grasp the leaflets to be fastened. For instance, a hook as shown in FIG. 23 can be used to grab one leaflet while jaws such as shown in FIGS. 19A-D can be used to grab the other leaflet. As another example, two sets of jaws can be used, each grabbing one leaflet.

Figure 24:
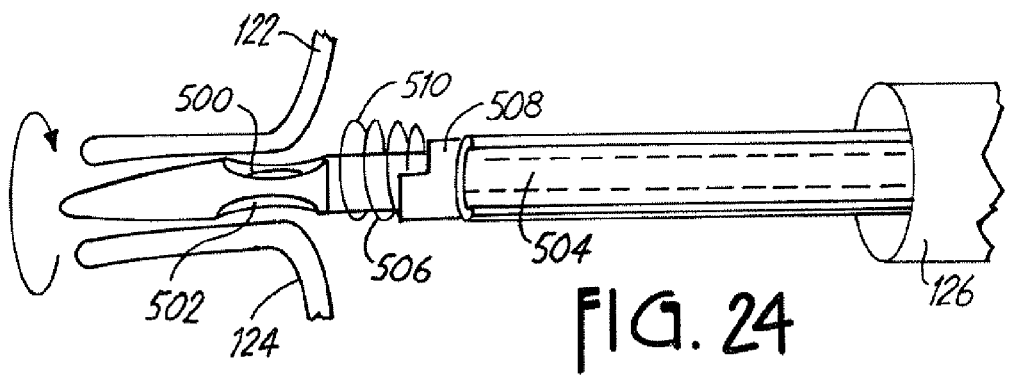
FIG. 24 is a side view of a spring fastener with a suction based gripper.

With respect to fastener applicators, a spring fastener embodiment is depicted in FIGS. 24-25. Leaflets 122, 124 are drawn into cavities 500, 502 with suction similar to that applied by the device in FIG. 16. Vacuum is applied by way of lumen 504. Spring 506 is pushed and rotated using rotating shaft 508. End 510 of spring 506 catches a leaflet such that rotating the spring 506 causes spring 506 to spiral through leaflets 122, 124 as shown in FIG. 25, fastening leaflets 122, 124 together. After spring 506 is placed through the leaflets, vacuum is released and lumen 504 is withdrawn.

Referring to FIGS. 26-33, another embodiment of a fastener applicator uses a fastener clip button 540 which includes a first portion 542 and a second portion 544. Referring to FIGS. 28 and 29, first portion 542 includes spikes 546 extending from a first surface 548 of base 550. Base 550 has notches 552 at the edge of second surface 554 at a position rotated 90 degrees relative to spikes 546. The center of base 550 has an opening 556 with wings 558 oriented toward notches 552. Second surface 554 includes indentations 560 adjacent opening 556 oriented toward spikes 546.

Referring to FIGS. 30-32, second portion 544 includes perforations 566 which have a diameter equal to or slightly smaller than spikes 546. Tabs 568 extend from first surface 570 of base 572. Tabs 568 include lips 574 that can engage notches 552. Base 572 includes an opening 578 with wings 580. Base 572 is slightly noncircular to allow for tabs 568.

FIG. 33 displays first portion 542 engaged with second portion 544. When portions 542, 544 are engaged, spikes 546 engage perforations 566 and tabs 568 engage notches 552. The leaflets are positioned in the separation between base 550 and base 572.

Referring to FIG. 26, to deploy clip button 540, first portion 542 is positioned with first applicator 580. First applicator 580 includes a central core 582 with a knob 584 at the end of the central core 582, as shown in FIG. 26A. Knob 584 engages indentations 560 when first portion is positioned on first applicator 580, and can pass through wings 558 when oriented accordingly for removal of first applicator 580. First applicator 580 also includes tubular portion 588, which slides over central core 582. When knob 584 engages indentations 560 and tubular portion 588 engages first surface 548, first portion 542 is held firmly by first applicator 580. Preferably, first portion 542 is placed in position near the leaflets prior to grasping of the leaflets by a gripper. Once grasped, the leaflets can be pierced with spikes 546 of first portion 542.

After spikes 546 are inserted through the leaflets, tubular portion 588 can be removed through cardiac catheter 126. Then, second applicator 590 can be slid over central core 582, as shown in FIG. 27. Second applicator 590 is used to engage second portion 544 with first portion 542. Second applicator 590 can push second portion 544 into place, or, alternatively, second applicator 590 can hold second portion 544 using a fastener such as threads or a clamp, as first portion 542 is pulled against it. After second portion 544 engages first portion 542, second applicator 590 is removed through cardiac catheter 126. Central core 582 is removed by first rotating knob 584 such that knob 584 passes through wings 558 and 580. Clip button 540 remains fastened to the mitral valves leaflets.

Figure 34:
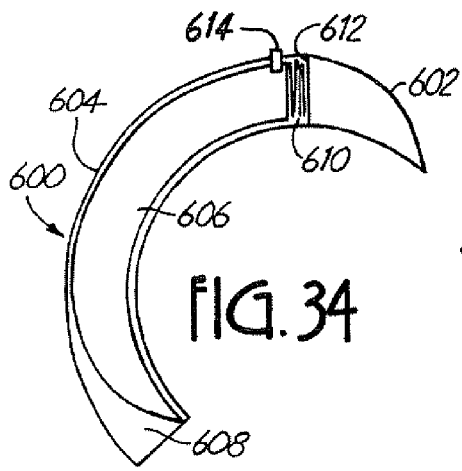
FIG. 34 is a sectional side view of a spring loaded ring in a loaded position.
Figure 35:
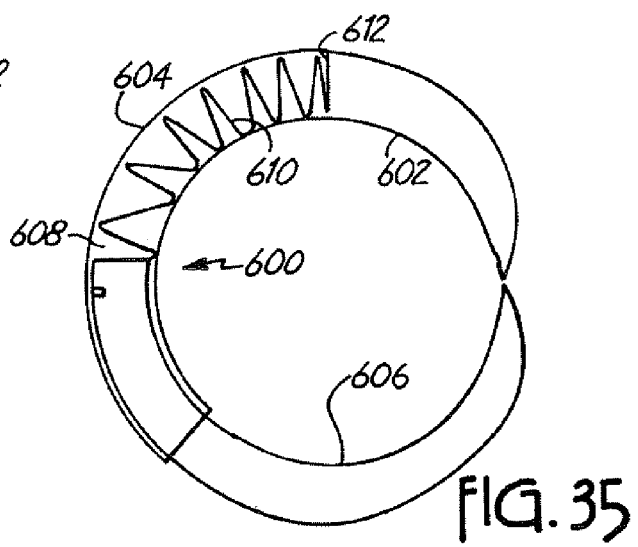
FIG. 35 is a sectional side view of the spring loaded ring of FIG. 34 in an extended position.

Another embodiment of a fastener uses a deformable ring. Different variations of the ring are available. A first embodiment of a spring loaded ring is depicted in FIGS. 34 and 35. Spring loaded ring 600 has a first spike 602 at the end of crescent portion 604. Second spike 606 is initially located in cavity 608 within crescent portion 604. Spring 610 is located between second spike 606 and surface 612. A button lock 614 holds second spike 606 within crescent portion 604 until deployment of spring loaded ring 600. When the lock 614 is released, first spike 602 and second spike 606 pierce the leaflets and secure them together. Alternative embodiments of the spring loaded ring can employ dual springs with a spike being propelled by each spring. If desired, the spikes can be retractable such that the ring is used to hold the leaflets while another fastening approach is used to secure the leaflets.

Figure 36:
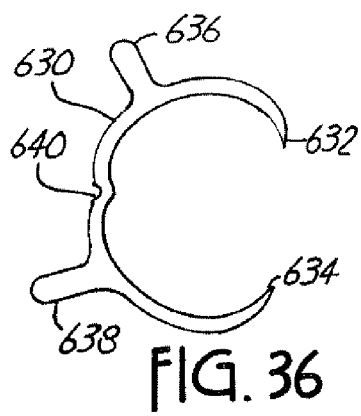
FIG. 36 is a side view of a crimp ring in an uncrimped position.
Figure 37:
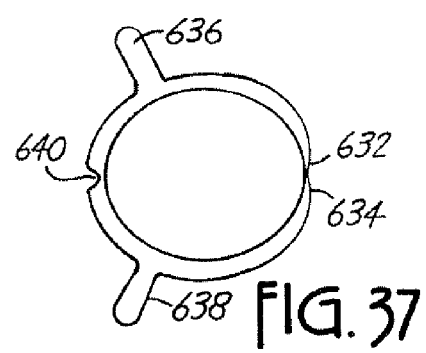
FIG. 37 is a side view of the crimp ring of FIG. 36 following crimping.

Referring to FIGS. 36 and 37, crimp ring 630 includes points 632, 634 and handles 636, 638. Between handles 636, 638 is a notch 641. Notch 640 provides a weak location for bending points 632, 634 toward each other, as shown in FIG. 37. Crimp ring 630 is placed near the grasped leaflet. Then, handles 636, 638 are rotated away from each other to place the crimp ring 630 in the closed crimped position shown in FIG. 37 with points 632, 634 piercing respective leaflets.

Figure 39:
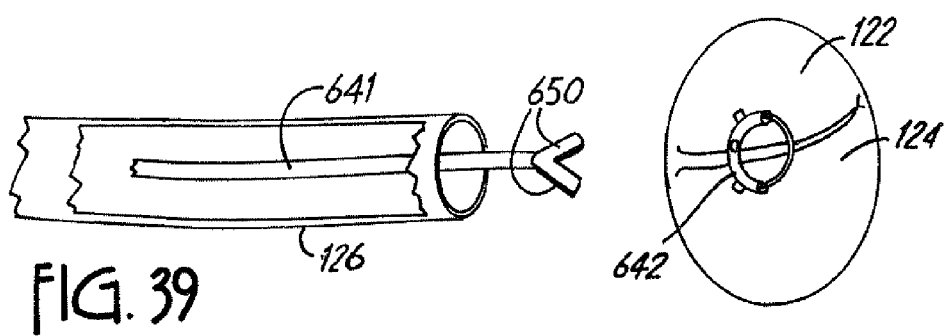
FIG. 39 is a perspective view of the applicator of FIG. 38 following deployment of the ring fastener.
Figure 38:
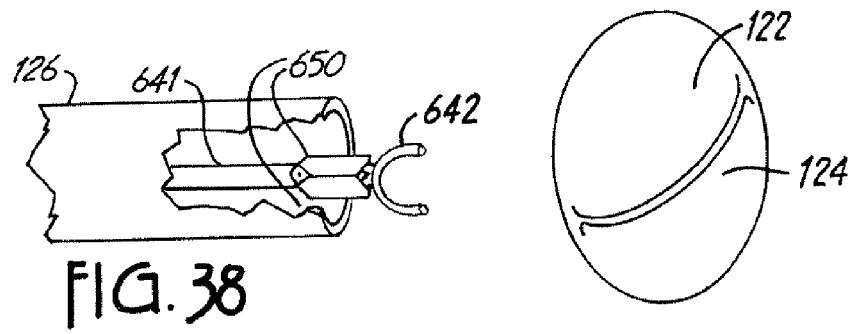
FIG. 38 is a perspective view of a ring fastener being positioned with an applicator toward heart valve leaflets, where a portion of the cardiac catheter is cut away to permit the visibility of structure within the catheter.
Figure 40:
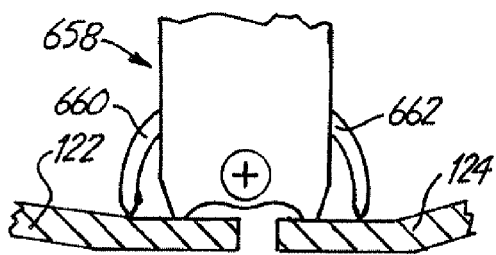
FIG. 40 is a side view of one embodiment of an automatic suture device positioned near heart valve leaflets.
Figure 41:
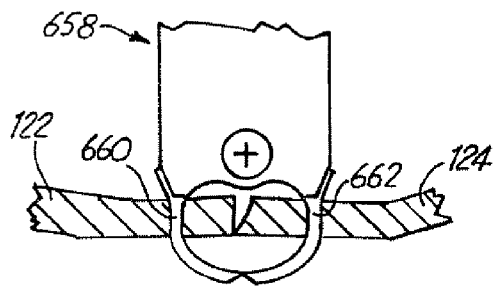
FIG. 41 is a side view of the automatic suture device of FIG. 40 gripping the heart valve leaflets with needles.
Figure 42:
FIG. 42 is a sectional view of one of the needles of the automatic suture device of FIG. 40.
Figure 43:
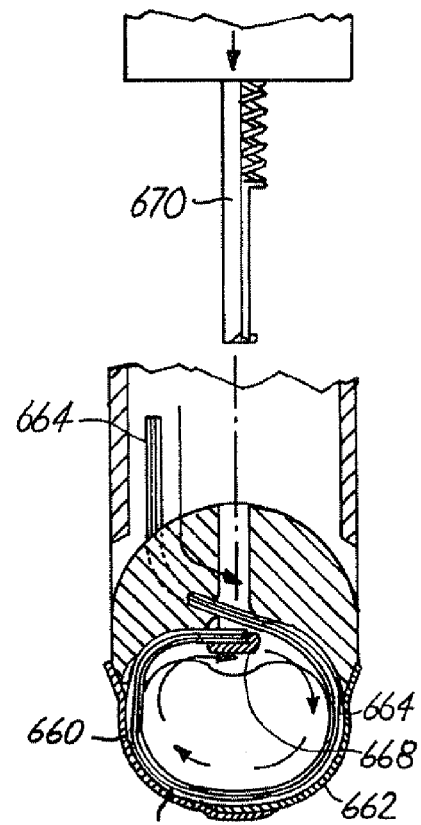
FIG. 43 is sectional view of the automatic suture device of FIG. 40 with an ultrasonic welder positioned for placement at its ultimate welding position.

Rings such as spring loaded ring 600 and crimp ring 630 can be applied with an applicator 641, as depicted in FIGS. 38 and 39. Ring 642 is brought up to leaflets 122, 124 and deformed to pierce leaflets 122, 124. Applicator 641 can include lever arms 650 and/or other implements to assist with deployment of rings 600 or 630. For example, for spring loaded ring 600, either lever arms 650 or another implement releases lock 614. For crimp ring 630, lever arms 650 hold handles 636, 638 and rotate handles to crimp the ring to bring points 632, 634 toward each other.

An automatic suture device can be used as a fastener. One embodiment of an automatic suture device is described in U.S. Pat. No. 5,417,700, to Egan, incorporated herein by reference. Referring to FIGS. 40-43, suture device 658 includes hollow needles 660, 662, which can rotate to pierce leaflets 122, 124. Suture 664 (FIG. 43) is threaded through channel 666 (FIG. 42) within hollow needles 660, 662. Suture 664 can be secured with an ultrasonic weld formed between weld anvil 668 and welding horn 670. Suture 664 can be pulled tight prior to welding.

Figure 44:
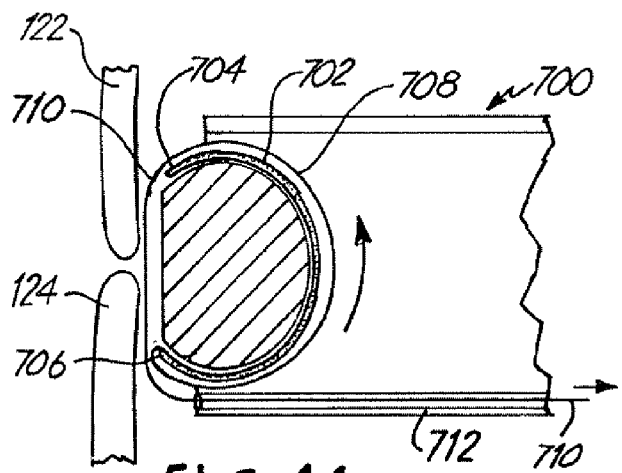
FIG. 44 is a side view of an alternative embodiment of an automatic suture device.
Figure 45:
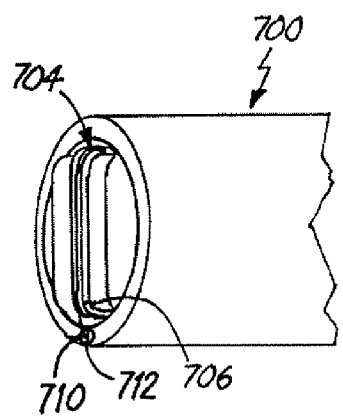
FIG. 45 is a perspective view of the automatic suture device of FIG. 44.

An alternative embodiment of an automatic suture device is shown in FIGS. 44 and 45. The suture device 700 includes a curved needle 702. Needle 702 has a point 704 and a blunt end 706. Needle 702 lies within slot 708. Suture 710 is threaded through channel 712. Suture 710 exits channel 712, crosses to the opposite opening into slot 708, circumscribes slot 708 and attaches to needle 702 at blunt end 706.

Suture 710 is pulled, which rotates needle 702, impaling leaflets 122, 124 with point 704. Needle 702 is rotated about 360 degrees such that needle 702 has passed through leaflets 122, 124. Following complete rotation of needle 702, suture 710 is threaded through leaflets 122, 124. Withdrawal of suture device 700 through the catheter introducer pulls suture 710 through leaflets 122, 124. Suture 710 can be tied, as described above with respect to FIG. 3, to secure leaflets 122, 124. Alternatively, a suture clip 132 can be used to secure suture 710, as shown in FIG. 5.

All of the devices described above can be constructed from standard biocompatible materials including a variety of metals, such as stainless steel and titanium, and polymers, such as polysulfone. The materials can be selected as appropriate for a particular application. Furthermore, the fasteners can be coated with a surface modifier such as polytetrafluoroethylene (PTFE), i.e., Teflon®, or an antimicrobial coating, such as silver metal or a silver compound. Antimicrobial metal coatings are further described in copending and commonly assigned U.S. patent application Ser. No. 08/974,992 to Ogle et al., entitled "Medical Article with Adhered Antimicrobial Metal," incorporated herein by reference.

Surgical Procedure

In preferred embodiments of the procedure, the repairs are performed on a beating heart. Alternatively, the heart can be stopped during the procedure. Cardioplegia, i.e., stopped cardiac contraction, can be induced by certain chemicals such as cold potassium-containing solutions that are introduced into the myocardium. The chemical induction of cardioplegia requires the isolation of the heart and ascending aorta from the rest of the patient's vascular system. Procedures using cardioplegia are less desirable since they require cardiopulmonary bypass, which increases patient risk factors.

For cardiac catheter based embodiments, one or more access points are used along the patient's chest, generally positioned between adjacent ribs. The access points provide access to the heart. Incisions are made to initiate the access points. Trocar sheaths, such as those used for the performance of laparoscopic procedures, can facilitate use of the access points as described in published PCT application WO 94/18881 to Stanford Surgical Technologies, Inc., incorporated herein by reference. Alternatively, soft tissue retractors, such as those used in pediatric open chest procedures can be utilized to facilitate use of the access points. Suitable location of the access point(s) can be determined based on the approach appropriate for the gripper/fastener applicator to be used.

Once the heart is accessed, a guide wire can be inserted through the wall of the heart either near the apex of the heart into the left ventricle or near the top of the heart into the left atrium. A dilator can be slid over the guide wire to expand the opening into the heart. Suitable guidewires and dilators are available from Daig Corp., Minnetonka, Minn. A cardiac catheter with a hemostasis valve, described above, is deployed over the dilator. The cardiac catheter provides access into the heart to deliver the repair device or devices.

Alternatively, a cardiac catheter can be inserted through an incision in the wall of the heart at the desired location. As during normal cannulation, a purse string suture can be applied at the point where the cardiac catheter enters the heart to reduce any bleeding. The suture can be applied, for example, using a piece of suture with a needle on both ends. The needles can be manipulated using forceps or the like. After the desired stitching is performed, the needles can be cut off using endoscopic scissors. Additional cardiac catheters can be placed near or into the heart, as desired.

Once the cardiac catheter is in place, the gripper/fastener instruments can be directed at the mitral or tricuspid valve to perform the repair. All of the instruments are designed such that the appropriate manipulations by the appropriate health care professional are performed at the proximal end of the cardiac catheter.

Following completion of the bow-tie repair, the cardiac catheter is removed. The procedures used to deploy the cardiac catheter preferably minimize the damage to the heart muscle by separating the tissue without significantly tearing the tissue. Nevertheless, stitches or staples can be used to close the incision at the point where the cardiac catheter was inserted. Once access to the heart has been closed, the incision providing access into the chest cavity is closed.

Alternatively, a less invasive, percutaneous vascular approach can be used. There are two, alternative, percutaneous vascular approaches to positioning the catheter for the medical procedure. One is to introduce the catheter into the femoral artery by a standard introducer sheath and advance it up the aorta, across the aortic valve into the left ventricle and then position its tip under the mitral annulus. This is commonly referred to as the "retrograde" approach.

The other approach, commonly referred to as the transseptal approach, is to introduce a transseptal sheath apparatus, a long single plane curve introducer, into the right femoral vein and advance it through the inferior vena cava into the right atrium. A puncture is then made through the fossa ovalis in the intraatrial septum, and the apparatus is advanced into the left atrium where the trocar and dilator of the apparatus is removed, leaving the sheath in position in the left atrium. Once the valve is accessed, the repair can be completed as described above.

Edge-to-edge mitral valve repair provides a simple and effective repair technique relative to complex and surgically demanding approaches of chordal shortening, resectioning, chordal transposition or artificial chordae replacement. The edge-to-edge repair is particularly effective with severe isolated mitral regurgitation or in association with coronary artery bypass surgery. The present approach provides the benefits of the edge-to-edge repair without the trauma of open heart surgery and cardiopulmonary bypass. Thus, the procedure can be accomplished concomitant with coronary artery bypass graft (CABG) or as a stand alone outpatient procedure in a cardiac catheterization laboratory. The advantages include reduced cost, hospitalization and patient recovery times. With minimal trauma to the patient, it may be desirable to perform the repair earlier before the disease has progressed to a serious level. Thus, more repair procedures may be performed, preventing further progression of the disease, obviating the need for more serious invasive procedures.

The instruments described above may be distributed in the form of a kit. Generally, the kit includes a fastener applicator and a suitable cardiac catheter or other catheter for a vascular approach. The kit may also include a suitable gripper for use with the fastener applicator. Alternatively, the kit may include only a fastener (fastener applicator) and/or a gripper. The kit preferably includes instructions for the performance of mitral and/or tricuspid valve repair. In particular, the instructions can describe the particular use of the fastener applicator and/ or the grippers.

Although the present invention has been described with reference to preferred embodiments, workers skilled in the art will recognize that changes may be made in form and detail without departing from the spirit and scope of the invention.

What is claimed is:

1. A heart valve leaflet fastener comprising at least one pair of arms, at least one arm of the pair of arms having a tapered protrusion extending toward the other arm of the pair of arms and the other arm of the at least one pair of arms having a tapered slot for accepting the tapered protrusion therein for fastening two adjacent tissue heart valve leaflets, wherein the arms pivot from one orientation to a gripping position with ends of respective paired arms being directed toward each other such that the tapered protrusion positions within the tapered slot to grip the two adjacent tissue heart valve leaflets.

2. A kit comprising a cardiac catheter, a fastener applicator and a leaflet fastener of claim 1, the cardiac catheter having suitable dimensions for deployment and insertion into a human heart in the vicinity of the mitral or tricuspid valve, the leaflet fastener having a size allowing insertion through the cardiac catheter, the fastener applicator releasably holding the leaflet fastener.

3. The kit of claim 2 wherein the paired arms comprise gripping elements that extend toward each other when the fastener is in a gripping position.

4. The kit of claim 2 wherein the arms flex to a low profile position to fit within the cardiac catheter.

5. The kit of claim 2 wherein the arms pivot between a low profile position and an unconstrained extended position.

6. The kit of claim 2 wherein the fastener applicator comprises a shaft and a bayonet fastener that releasably holds the leaflet fastener on the shaft.

7. The kit of claim 2 wherein the fastener applicator comprises a shaft and a latch that releasably holds the leaflet fastener on the shaft.

8. A device comprising a catheter, a leaflet fastener applicator and a leaflet fastener of claim 1, the catheter having a proximal end, a distal end and suitable dimensions for insertion into a heart, the leaflet fastener applicator passing through the catheter being actuatable from the proximal end of the catheter and a fastening element projecting from the distal end of the catheter, the leaflet fastener applicator releasably holding the leaflet fastener.

9. A heart valve repair instrument comprising a shaft, a cap, a gripper and a flexible rod, wherein the gripper comprises a plurality of arms radiating from a pivot with each arm having a spike, wherein the cap is located distal to the pivot and the pivot is located distal to the shaft, and wherein the flexible rod connects to the cap to provide for movement of the cap relative to the pivot of the gripper and the shaft by pulling the flexible rod, the cap having an opening that can be positioned over the pivot to lock the arms in a closed position.

10. The instrument of claim 9 wherein the pivot is formed from spring metal or memory metal.

11. The instrument of claim 10 wherein the memory metal comprises a nickel alloy.

12. The instrument of claim 10 wherein the memory metal is selected from the group consisting of cobalt-chromium-nickel-molybdenum alloy, MP35N, nickel-titanium alloy, stainless steel and spring metal.

13. The instrument of claim 10 wherein the plurality of arms comprises two pairs of arms wherein pairs of arms are connected by a resilient web.

14. The instrument of claim 13 wherein the web is covered with fabric.

15. The instrument of claim 9 wherein the pivot comprises a hinge.

16. The instrument of claim 15 wherein the hinge comprises a spring.

17. The instrument of claim 9 wherein the flexible rod has a disengaging mechanism that releasably connects the cap to the rod.

18. The instrument of claim 9 wherein the arms are biased to an extended position due to expansive forces at the pivot and further comprising strands that connect the shaft with the arms to constrain the extension of the arms.

19. The instrument of claim 9 wherein the cap comprises a ridge and the gripper comprise a bump positioned to engage the ridge in the locked position.

20. A fastening member comprising a cap and a gripper configured to grip a tissue heart valve leaflet, the cap being slideable relative to the gripper, wherein the gripper comprises a plurality of arms radiating from a pivot, with at least a first arm having a tapered spike, and at least a second arm having a plurality of spikes such that a tapered slot is formed between the plurality of spikes, wherein the pivot is inserted within an opening in the cap to lock the arms in a collapsed gripping position such that the tapered spike positions within the tapered slot.

21. The fastening member of claim 20 wherein the cap comprises a locking mechanism that engages the gripper to lock the gripper in a locked position.

22. The fastening member of claim 20 wherein the cap comprises a slot, and wherein the gripper is held by stops within the slot such that the gripper can slide within the slot to alter the extension of the gripper with the stops preventing separation of the cap and gripper.

23. A kit comprising the fastening member of claim 20 and a flexible rod, the flexible rod has a disengaging mechanism that permits the flexible rod to releasably hold the cap.

* * * * *